(12) United States Patent
Greenberger et al.

(10) Patent No.: US 8,445,261 B2
(45) Date of Patent: *May 21, 2013

(54) APPARATUS FOR HOLDING CELLS

(75) Inventors: Joel S. Greenberger, Sewickley, PA (US); Paul A. DiMilla, Gibsonia, PA (US); Michael M. Domach, Pittsburgh, PA (US); Raymond K. Houck, Oakmont, PA (US)

(73) Assignee: University of Pittsburgh, Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/930,471

(22) Filed: Jan. 7, 2011

(65) Prior Publication Data
US 2011/0195055 A1    Aug. 11, 2011

Related U.S. Application Data

(62) Division of application No. 09/292,056, filed on Apr. 14, 1999, now Pat. No. 7,867,752, which is a division of application No. 08/741,628, filed on Nov. 1, 1996, now Pat. No. 6,008,010.

(51) Int. Cl.
*C12M 1/36* (2006.01)
*C12M 1/34* (2006.01)

(52) U.S. Cl.
USPC .......... 435/286.1; 435/286.4; 435/287.3; 435/288.4; 435/288.7; 435/303.1; 435/809

(58) Field of Classification Search
USPC .................. 435/287.3, 288.7, 303.1, 809
See application file for complete search history.

(56) References Cited

U.S. PATENT DOCUMENTS

| | | | |
|---|---|---|---|
| 4,344,816 | A | 8/1982 | Craighead et al. |
| 4,647,531 | A | 3/1987 | Kamentsky |
| 4,673,988 | A | 6/1987 | Jansson et al. |
| 4,676,951 | A | 6/1987 | Armes et al. |
| 4,711,851 | A | 12/1987 | McNamara et al. |
| 4,762,701 | A | 8/1988 | Horan et al. |
| 4,783,401 | A | 11/1988 | Horan et al. |
| 4,859,584 | A | 8/1989 | Horan et al. |
| 5,031,099 | A | 7/1991 | Kettler |
| 5,072,382 | A | 12/1991 | Kamentsky |

(Continued)

FOREIGN PATENT DOCUMENTS

| | | |
|---|---|---|
| JP | 58155087 A | 9/1983 |
| JP | 05049467 A | 2/1993 |

OTHER PUBLICATIONS

James P. Freyer, et al., "A Simple Electronic Volume Cell Sorter for Clonogenicity Assays," Cytometry, (vol. 10), p. 273-281, (1989).

(Continued)

*Primary Examiner* — William H Beisner
(74) *Attorney, Agent, or Firm* — Ansel M. Schwartz

(57) ABSTRACT

An apparatus for holding cells. The apparatus comprises a mechanism for incubating cells having a dynamically controlled environment in which the cells are grown, which are maintained in a desired condition and in which cells can be examined while the environment is dynamically controlled and maintained in the desired condition. The apparatus also comprises an imaging mechanism for automatically determining the state of an individual cell of the cells over time. The imaging mechanism is in communication with the incubating mechanism.

17 Claims, 13 Drawing Sheets

U.S. PATENT DOCUMENTS

| | | | |
|---|---|---|---|
| 5,107,422 A | | 4/1992 | Kamentsky et al. |
| 5,162,204 A | | 11/1992 | Matsuzaki et al. |
| 5,310,674 A | | 5/1994 | Weinreb et al. |
| 5,355,215 A | | 10/1994 | Schroeder et al. |
| 5,403,735 A | | 4/1995 | Maruhashi et al. |
| 5,548,661 A | | 8/1996 | Price et al. |
| 5,612,188 A | | 3/1997 | Shuler et al. |
| 5,670,113 A | | 9/1997 | Akong et al. |
| 5,732,150 A | | 3/1998 | Zhou et al. |
| 5,790,710 A | | 8/1998 | Price et al. |
| 5,885,840 A | | 3/1999 | Kamentsky et al. |
| 6,008,010 A | * | 12/1999 | Greenberger et al. .......... 435/41 |
| 6,103,479 A | | 8/2000 | Taylor |
| 6,416,959 B1 | | 7/2002 | Giuliano et al. |
| 7,867,752 B1 | * | 1/2011 | Greenberger et al. ..... 435/286.1 |

OTHER PUBLICATIONS

N. M. McKenna and Y.-L. Wang, "Culturing Cells on the Microscope Stage," Fluorescence Microscopy of Living Cells in Culture, Part A, Methods in Cell Biology, Academic Press, Inc., (vol. 29), (p. 195-205), (1989).

Y.-L. Wang and D. Lansing Taylor Eds., Academic Press (San Diego), (p. 108-111), (1989).

Hartmann-Petersen R., Walmod, P., "Individual cell motility studies by time-lapse video recording: Influence of experimental conditions," Cytometry, p. 260-270, (2000).

Bodin, P., Papin, S., Meyer, C., Travo, P. "Study of living single cells in culture: automated recognition of cell behavior," Lab Invest., vol. 59 (No. 1), p. 137-43, (Jul. 1988).

Koichi Ikuta and Irving L. Weissman, "Evidence that hematopoietic stem cells express mouse c-kit but do not depend on steel factor for their generation," Proc. Natl. Acad. Sci. USA, vol. 89, p. 1502-1506 (Feb. 1992) Medical Sciences.

I.D. Bernstein, R.G. Andrews, K.M. Zsebo, "Recombinant Human Stem Cell Factor Enhances the Formation of Colonies by CD34+ and CD34+lin− Cells, and the Generation of Colony-Forming Cell Progeny From CD34+lin− Cells Cultured With Interleukin-3, Granulocyte Colony-Stimulating Factor, or Granulocyte-Macrophage Colony-Stimulating Factor," Blood, vol. 77, No. 11 (Jun. 1, 1991), p. 2316-2321.

J.P. Goff, D.S. Shields, B.E. Petersen, V.F. Zajac, G.K. Michalopoulos, J.S. Greenberger, "Synergistic Effects of Hepatocyte Growth Factor on Human Cord Blood CD34+ Progenitor Cells are the Result of c-met Receptor Expression," Stem Cells 1996, 14:592-602.

M. Musashi, Yu-Chung Yang, S.R. Paul, S.C. Clark, T. Sudo and M. Ogawa, "Direct and synergistic effects of interleukin 11 on murine hemopoiesis in culture," Proc. Natl. Acad. Sci USA, vol. 88, p. 765-769, Feb. 1991 Cell Biology.

K. Ikebuchi, G.G. Wong, S.C. Clark, J.N. Ihle, Y. Hirai, and M. Ogawa, "Interleukin 6 enhancement of interleukin 3-dependent proliferation of multipotential hemopoietic progenitors," Proc. Natl. Acad. Sci. USA, vol. 84, p. 9035-9039, Dec. 1987 Cell Biology.

S. Miltenyi, S. Guth, A. Radbruch, E. Pfluger, A. Thiel, "Isoloation of CD34+ Hematopoietic Progenitor Cells by High-Gradient Magnetic Cell Sorting (MACS)," AlphaMed Press, p. 201-213.

Malcom A.S. Moore, "Clinical Implications of Positive and Negative Hematopoietic Stem Cell Regulators," The Journal of the American Society of Hematology, Jul. 1, 1991, p. 1-19.

H.J. Sutherland, P.M. Lansdorp, D.H. Henkelman, A.C. Eaves, and C.J. Eaves, "Functional characterization of individual human hematopoietic stem cells cultured at limiting dilution on supportive marrow stromal layers," Proc. Natl. Acad. Sci. USA, vol. 87, p. 3584-3588, May 1990, Medical Sciences.

K. Pogue-Geile, Mary Ann Sakakeeny, J.L. Panza, S.L. Sell, and J.S. Greenberger, "Cloning and Expression of Unique Murine Macrophage Colony-Stimulating Factor Transcripts," Blood, vol. 85, No. 12, p. 3478-3486, Jun. 15, 1995.

H. Ogata, W.G. Bradley, M. Inaba, N. Ogata, S. Ikehara and R.A. Good, "Long-term repopulation of hematolymphoid cells with only a few hemopoietic stem cells in mice," Proc. Natl. Acad. Sci. USA, vol. 92, p. 5945-5949, Jun. 1995 Immunology.

G. Van Zant, S.A. Rummel, M.R. Koller, D.B. Larson, I. Drubachevsky, M. Palsson, and S.G. Emerson, "Expansion in Bioreactors of Human Progenitor Populations from Cord Blood and Mobilized Peripheral Blood," Blood Cells (1994) 20:482-491.

C.M. Verfaillie, "Can Human Hematopoietic Stem Cells Be Cultured Ex Vivo?," Stem Cells, 1994; 12:466-476.

C.M. Traycoff, S.T. Kosak, S. Grigsby, and E.F. Srour, "Evaluation of Ex Vivo Expansion Potential of Cord Blood and Bone Marrow Hematopoietic Progenitor Cells Using Cell Tracking and Limiting Dilution Analysis," The American Society of Hematology, 1995, p. 2059-2068.

H. Mayani, P.M. Lansdorp, "Proliferation of individual hematopoietic progenitors purified from umbilical cord blood," Experimental Hematology, 23:1453-1462 (1995).

C.L. Li and G.R. Johnson, "Murine Hematopoietic Stem and Progenitor Cells: I. Enrichment and Biologic Characterization," Blood, vol. 85, No. 6, p. 1472-1479, (Mar. 15, 1995).

C.E. Sandstrom, J.G. Bender, E.T. Papoutsakis, and W.M. Miller, "Effects of CD34+ Cell Selection and Perfusion on Ex Vivo Expansion of Peripheral Blood Mononuclear Cells," Blood, vol. 86, No. 3, p. 958-970, (Aug. 1, 1995).

C.M. Verfaillie, P.M. Catanzarro, and Wen-na Li, "Macrophage Inflammatory Protein 1α, Interleukin 3 and Diffusible Marrow Stromal Factors Maintain Human Hematopoietic Stem Cells for at least Eight Weeks in Vitro," The Rockefeller University Press, vol. 179, p. 643-649, Feb. 1994.

E.D. Zanjani, G. Almeida-Porada, A.W. Flake, "Retention and Multilineage Expression of Human Hematopoietic Stem Cells in Human-Sheep Chimeras," Stem Cells, 1995, 113:101-111.

Donald Metcalf, "Hematopoietic Regulators: Redundancy or Subtlety?," Blood, vol. 82, No. 12, p. 3515-3523, Dec. 15, 1993.

M. Musashi, S.C. Clark, T. Sudo, D.L. Urdal, and M. Ogawa, "Synergistic Interactions Between Interleukin-11 and Interleukin-4 in Support of Proliferation of Primitive Hematopoietic Progenitors of Mice," Blood, vol. 78, No. 6, p. 1448-1451, Sep. 15, 1991.

N. Uchida, H.L. Aguila W.H. Fleming, L. Jerabek, and I.L. Weissman, "Rapid and Sustained Hematopoietic Recovery in Lethally Mice Transplanted With Purified Thy-1.1$^{lo}$ Lin− Sca-1+ Hematopoietic Stem Cells," Blood, vol. 83, No. 12, p. 3758-3779, Jun. 15, 1994.

L. Rothstein, J.H. Pierce, V. Klassen, and J.S. Greenberger, "Amphotropic Retrovirus Vector Transfer of the v-ras Oncogene to Human Hematopoietic and Stromal Cells in Continuous Bone Marrow Cultures," Blood, vol. 65, No. 3, p. 744-752, (Mar. 1985).

C. Issaad, L. Croisille, A. Katz, W. Vainchenker, and L. Coulombel, "A Murine Stromal Cell Line Allows the Proliferation of Very Primitive Human CD34++/CD38− Progenitor Cells in Long-Term Cultures and Semisolid Assays," The American Society of Hematology, 1993, p. 2916-2924.

R. Pettengell, T. Luft, R. Henschler, J.M. Hows, T.M. Dexter, D. Ryder, and N.G. Testa, "Direct Comparison by Limiting Dilution Analysis of Long-Term Culture-Initiating Cells in Human Bone Marrow, Umbilical Cord Blood, and Blood Stem Cells," Blood, vol. 84, No. 11 (Dec. 1, 1994), p. 3653-3659.

Joel S. Greenberger, "Recent Modifications of Technique in Human Long-Term Bone Marrow Cultures," Long-Term Bone Marrow Culture, p. 119-131 (1984).

Joel S. Greenberger, "Long-Term Hematopietic Cultures," p. 203-242.

G. Migliaccio, A.R. Migliaccio, M.L. Druzin, Patricia-Jane V. Giardina, K.M. Zsebo, and J.W. Adamson, "Long-Term Generation of Colony-Forming Cells in Liquid Culture of CD34+ Cord Blood Cells in the Presence of Recombinant Human Stem Cell Factor," Blood, vol. 79, No. 10 (May 15, 1992), p. 2620-2627.

Ronald Kline, "New Marrow for Old," Technology Review, 1996, p. 43-49.

Joel S. Greenberger, "The hematopoietic microenvironment," Critical Reviews in Oncology/Hematology, 1991, 11:65-84, 1991.

T.W. Thomas and P.A. DiMilla, "Effects of Substratum Compliance on the Motility, Morphology, and Proliferation of Adherent Human Gliablastoma Cells," In Proceedings of the 1995 Bioengineering Conference, BED—vol. 29, R.M. Hochmuth, N.A. Langrana, and M.S. Hefzy, eds., ASME, New York, p. 153-154, (1995).

Inside Surgery "Organ and Tissue Transplant Update," Medical Data International, Inc., vol. III: No. 8, Feb. 1996.

P.A. DiMilla, "Receptor-Mediated Adhesive Interactions at the Cytoskeleton/Substratum interface During Cell Migration," In Cell Mechanics and Cellular Engineering, R.M. Hochmuth, V.C. Mow, F. Guilak, and R. Tran-Son-Tay, eds., Springer-Verlag, New York, p. 490-415, 1994.

P.A. DiMilla, J.A. Stone, S.M. Albelda, D.A. Lauffenburger, and J.A. Quinn, "Measurement of Cell Adhesion and Migration on Protein-Coated Surfaces," Mat. Res. Soc. Symp. Proc., vol. 252, 1992, p. 205-212.

P.A. DiMilla, J.A. Quinn, S.M. Albelda, D.A. Lauffenburger, "Measurement of Individual Cell Migartion Parameters for Human Tissue Cells," AICHE Journal, Jul. 1992, vol. 38, No. 7, p. 1092-1104.

P.A. DiMilla, J.A. Stone, J.A. Quinn, S.M. Albelda, and D.A. Lauffenburger, "Maximal Migration of Human Smooth Muscle Cells on Fibronectin and Type IV Collagen Occurs at an Intermediate Attachment Strength," The Rockefeller University Press, The Journal of Cell Biology, vol. 122, No. 3, Aug. 1993, p. 729-737.

J.P. Goff, D.S. Shields, G.K. Michalopoulos, and J.S. Greenberger, "Effects of Hepatocyte Growth Factor and IL-11 on Human Cord Blood $CD34^+$ Progenitor Cells," Abstracts, Aug. 31, p. 913.

J.P. Goff, D.S. Shields, G.K. Michalopoulos, and J.S. Greenberger, "Synergistic Effects of Hepatocyte Growth Factor on In Vitro Generation of CFU-GM from Human Cord Blood $CD34^+$ Progenitor Cells," Hematopoietic Growth Factors-III, p. 280a.

C.E. Dunbar, M. Cottler-Fox, J.A. O-Shaughnessy, S. Doren, C. Carter, R. Berenson, S. Brown, R.C. Moen, J. Greenblatt, F.M. Stewart, S.F. Leitman, W.H. Wilson, K. Cowan, N.S. Young, and A.W. Nienhuis, "Retrovirally Marked CD34-Enriched Peripheral Blood and Bone Marrow Cells Contribute to Long-Term Engraftment After Autologous Transplantation," Blood, vol. 84, No. 11, p. 3048-3057 (Jun. 1, 1995).

L. Murray, B. Chen, A. Galy, S. Chen, R. Tushinski, N. Uchida, R. Negrin, G. Tricot, S. Jagannath, D. Vesole, B. Barlogie, R. Hoffman, and A. Tsukamoto, "Enrichment of Human Hematopoietic Stem Cell Activity in the $CD34^+Thy^-1^+Lin^-$ Subpopulation From Mobilized Peripheral Blood," Blood, vol. 84, No. 2, p. 368-378 (Jan. 15, 1995).

\* cited by examiner

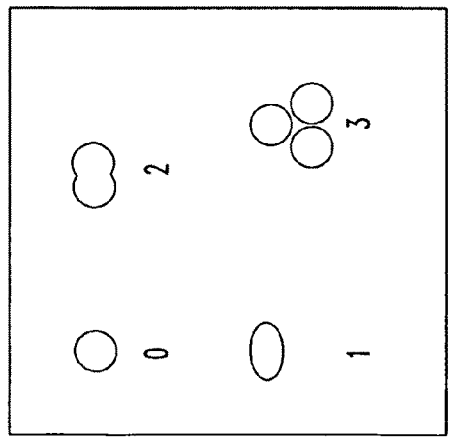

```
TOTAL NUMBER OF OBJECTS : 4

OBJECT NUMBER      0                OBJECT NUMBER      2
X CENTROID         100.000          X CENTROID         100.000
Y CENTROID         100.000          Y CENTROID         300.000
AREA IN PIXELS     20571            AREA IN PIXELS     17371
PERIMETER          161.252          PERIMETER          166.412
PERIM/AREA         1.043            PERIM/AREA         1.328
SPHERICITY         0.970            SPHERICITY         0.428
EXCENTRICITY       1.004            EXCENTRICITY       3.357

OBJECT NUMBER      1                OBJECT NUMBER      3
X CENTROID         312.500          X CENTROID         375.000
Y CENTROID         100.000          Y CENTROID         334.643
AREA IN PIXELS     32841            AREA IN PIXELS     61881
PERIMETER          213.180          PERIMETER          361.060
PERIM/AREA         1.135            PERIM/AREA         1.696
SPHERICITY         0.582            SPHERICITY         0.385
EXCENTRICITY       1.721            EXCENTRICITY       1.033
```

FIG.2 DEMONSTRATION OF PATTERN RECOGNITION FOR MODEL DATA. A. IMAGE OF "MODEL" DATA REPRESENTING 2 SINGLE CELLS, 1 DIVIDING CELL, AND 3 CELLS IN CONTACT. B. STATISTICS DETERMINED BASED ON IMAGE ANALYSIS OBJECTS 0 AND 2 HAVE A RELATIVELY SMALL AREAS AND ARE THE SINGLE CELLS ; OBJECT 1 HAS AN INTERMEDIATE AREA AND IS THE DIVIDING CELL ; OBJECT 4 HAS AN AREA ROUGHLY THREE TIMES AS LARGE AS OBJECTS 0 AND 2 AND IS THE CLUSTER .

US 8,445,261 B2

APPARATUS FOR HOLDING CELLS

CROSS-REFERENCE TO RELATED APPLICATIONS

This is a divisional of U.S. patent application Ser. No. 09/292,056 filed on Apr. 14, 1999, now U.S. Pat. No. 7,867,752 issued on Jan. 11, 2011, which is a divisional of U.S. patent application Ser. No. 08/741,628 filed Nov. 1, 1996, now U.S. Pat. No. 6,008,010 issued on Dec. 28, 1999, both of which are incorporated by reference herein.

FIELD OF THE INVENTION

The present invention is related to an apparatus for holding cells. More specifically, the present invention is related to an apparatus for incubating cells so that an array of single cells, or a functional ensemble, can be grown and individually analyzed in a dynamically controlled environment.

BACKGROUND OF THE INVENTION

In adult humans, hematopoeitic stem cells are found primarily in the bone marrow, although in newborns these cells also are present in the blood of the umbilical cord. Hematopoeitic stem cells are the progenitors (i.e., precursors) of mature blood cells in the body, and through a process called hematopoiesis, stem cells continuously regenerate the body's blood supply, including red blood cells (which transport oxygen in the body), white blood cells (which fight infections and comprise the body's immune system), and platelets (which form clots to stop bleeding). Hematopoiesis involves cell division (i.e., increase in cell number) and differentiation (i.e., change in cell phenotype). Chemotherapy and radiation therapy are important tools for treating patients with cancer or requiring solid-organ transplants, but these processes are (beneficially) toxic to the hematopoeitic (i.e., blood) system because chemotherapy and ionizing irradiation kill many of the stem cells in the bone marrow. This immunosuppression and other blood toxicity limit the effectiveness of many otherwise promising cancer therapies because a critical low number of blood cells in the body lead to life-threatening infection and bleeding.

Recovery from these therapies requires replenishment of the patient's stem cells. Treatment with growth factors currently is used to promote the recovery of blood cells but is only partially effective following immunosuppressive treatments. Alternatively, infusion of human stem cells through a bone marrow transplant increasingly is used by physicians to restore rapidly and permanently a patient's ability to regenerate blood cells. Transplants of bone marrow grew from 5,000 per year in 1990 to more than 40,000 per year by 1995 (Kline, Ronald, New Marrow for Old, Technology Review, November/December 1993, p. 43; Anonymous Inside Surgery, Medical Data International Ed., Vol. 3, No. 8, February 1996, p. 192). However, the large number of reports in the media citing people who are looking for appropriate bone marrow donors demonstrates that this process can be extremely difficult because appropriate donors are very rare in many cases. Although the best bone marrow donors are siblings, only 25% of the time is a sibling a compatible transplant donor (Kline, Ronald, New Marrow for Old, Technology Review, November/December 1993, p. 43).

The automated growth of stem cells through the use of a unique bioreactor system would be a very important advance for cancer research and therapy. For example, the use of the bioreactor system could eliminate the need for donors: some stem cells can be removed from a patient prior to chemotherapy, stored during chemotherapy, and then large numbers of stem cells generated in the bioreactor system can be transplanted back into the patient. This strategy cannot be implemented with current technologies for growing stem cells because these approaches predominantly result in hematopoeitic expansion to produce differentiated mature blood cells at the expense of increasing the number of pluripotent (most primitive) stem cells needed for long-term replenishment of the bone marrow (Van Zant, Gary, Rummel, Sue A., Koller, Manfred R., Larson, David B., Drubachevsky, Ilana, Palsson, Mahshid and Emerson, Stephen G. Expansion in Bioreactors of Human Progenitor Populations from Cord Blood and Mobilized Peripheral Blood. Blood Cells (1994) 20:482-491; Goff, Julie P., Shields, Donna S., Petersen, Bryon E., Zajac, Valerie F., Michalopoulos, George K. and Greenberger, Joel S. Synergistic Effects of Hepatocyte Growth Factor on Human Cord Blood CD34+ Progenitor Cells are the Result of c-met Receptor Expression. Stem Cells (In Press); Moore, MAS. Clinical Implications of Positive and Negative Hematopoeitic Stem Cell Regulators. Blood 1991; 78:1-19; Metcalfe, D. Hematopoeitic Regulators: Redundancy or Subtlety? Blood 1993; 82:3515-3523; Bernstein, I. D., Andrews, R. G., Zsebo, K. M. Recombinant Human Stem Cell Factor Enhances the Formation of Colonies by CD34+ and CD34+lin- Cells and the Generation of Colony-Forming Cell Progeny From CD34+lin- Cells Cultured With Interleukin-3, Granulocyte Colony-Stimulating Factor, or Granulocyte-Macrophage Colony-Stimulating Factor. Blood 1991; 77:2316-2321; Musashi, M. Clark, S. C., Suodo, T. et al. Synergistic Interactions Between Interleukin-11 and Interleukin-4 in Support of Proliferation of Primitive Hematopoeitic Progenitors of Mice. Blood 1991; 78:1448-1451; Musashi, M., Yang, Y-C, Paul, S. R. et al. Direct and Synergistic Effects of Interleukin-11 on Murine Hemopoiesis in Culture. Proc Natl Acad Sci 1991; 88:765-769; Migliaccio, G., Migliaccio, A. R., Druzin, M. L. et al. Long-Term Generation of Colony-Forming Cells in Liquid Culture of CD34+ Cord Blood Cells in the Presence of Recombinant Human Stem Cell Factor. Blood 1992; 79(10):2620-2627; Ikuta, K., Weissman, I. L. Evidence That Hematopoeitic Stem Cells Express Mouse C-Kit but do not Depend on Steel Factor for Their Generation. Proc Natl Acad Sci USA 1992; 89:1502-1506; Miltenyi, S., Guth, S., Radbruch, A. et al. Isolation of CD34+ Hematopoeitic Progenitor Cells by High-Gradient Magnetic Sorting. In: Wunder E., ed Hematopoeitic Stem Cells: Alpha Med Press 1994; 201-213; Traycoff, C. M., Kosak, S. T., Grigsby, S., Srour, E. F. Evaluation of Ex Vivo Expansion Potential of Cord Blood and Bone Marrow Hematopoeitic Progenitor Cells Using Cell Tracking and Limiting Dilution Analysis. Blood 85, No. 8:2059-2068 (Apr. 15, 1995); Murray, L., Chen, B., Galy, A., Chen, S., Tushinski, R., Uchida, N., Negrin, R., Tricot, G., Jagannath, S., Vesole, D., Barlogie, B., Hoffman, R., Tsukamoto, A. Enrichment of Human Hematopoeitic Stem Cell Activity in the CD34+Thy-1+Lin- Subpopulation from Mobilized Peripheral Blood. Blood 85, No. 2:368-378 (Jan. 15, 1995); Uchida, N., Aguila, H. L., Fleming, W. H., Jerabek, L., Weissman, I. L. Rapid and Sustained Hematopoeitic Recovery in Lethally Irradiated Mice Transplanted with Purified Thy-1.1 Lin- Sca1+ Hematopoeitic Stem Cells. Blood 83, No. 12:3758-3779 (Jun. 15, 1995).

The underlying biological problem is that differentiated daughter cells—termed "committed progenitors"—produce and secrete molecules that appear to inhibit the proliferation of nearby true stem cells (Ogata, H., Bradley, W. G., Inaba, M., Ogata, N., Ikehara, S., Good, R. A. Long-Term Repopulation of Hematolymphoid Cells With Only a Few Hemopoietic Stem Cells in Mice. Proc. Natl. Acad. Sci. USA. 92:5945-5949, June 1995; Li, C. L., Johnson, G. R. Murine Hematopoeitic Stem and Progenitor Cells: I. Enrichment and Biologic Characterization. Blood 85, No. 6:1472-1479 (Mar. 15, 1995); Dunbar, C. E., Cottler-Fox, M., O'Shaughnessy, J. A., Doren, S., Charter, C., Berenson, R., Brown, S., Moen, R. C., Greenblatt, J., Stewart, F. M., Leitman, S. F., Wilson, W. H., Cowan, K., Young, N. S., Nienhuis, A. W. Retrovirally Marked CD34-Enriched Peripheral Blood and Bone Marrow Cells Contribute to Long-Term Engraftment After Autologous Transplantation. Blood 85, No. 11:3048-3057 (Jun. 1, 1995); Traycoff, C. M., Kosak, S. T., Grigsby, S., Srour, E. F. Evaluation of Ex Vivo Expansion Potential of Cord Blood and Bone Marrow Hematopoeitic Progenitor Cells Using Cell Tracking and Limiting Dilution Analysis. Blood 85, No. 8:2059-2068 (Apr. 15, 1995); Murray, L., Chen, B., Galy, A., Chen, S., Tushinski, R., Uchida, N., Negrin, R., Tricot, G., Jagannath, S., Vesole, D., Barlogie, B., Hoffman, R., Tsukamoto, A. Enrichment of Human Hematopoeitic Stem Cell Activity in the CD34+Thy-1+Lin- Subpopulation from Mobilized Peripheral Blood. Blood 85, No. 2:368-378 (Jan. 15, 1995); Uchida, N., Aguila, H. L., Fleming, W. H., Jerabek, L., Weissman, I. L. Rapid and Sustained Hematopoeitic Recovery in Lethally Irradiated Mice Transplanted with Purified Thy-1.1 Lin-Sca1+ Hematopoeitic Stem Cells. Blood 83, No. 12:3758-3779 (Jun. 15, 1995); Issaad, C., Croisille, L., Katz, A., Vainchenker, W., Coulombel, L. A Murine Stromal Cell Line Allows the Proliferation of Very Primitive Human CD34+ +/CD38- Progenitor Cells in Long-Term Cultures and Semisolid Assays. Blood 81, No. 11:2916-2924 (Jun. 1, 1993); Pettengell, R., Luft, T., Henschler, R., Hows, J. M., Dexter, T. M., Ryder, D., Testa, N. G. Direct Comparison by Limiting Dilution Analysis of Long-Term Culture-Initiating Cells in Human Bone Marrow, Umbilical Cord Blood, and Blood Stem Cells. Blood 84, No. 11:3653-3659 (Dec. 1, 1994); Greenberger, J. S. Long-Term Hematopoeitic Cultures. In: Golde D, (ed). Methods in Hematology. New York: Churchill Livingston, 11:203-243, 1984; Rothstein, L., Pierce, J. H., Aaronson, S. A., Greenberger, J. S. Amphotropic Retrovirus Vector Transfer of the v-ras Oncogene Into Human Hematopoeitic and Stromal Cells in Continuous Bone Marrow Culture. Blood. 65:744-752, 1985; Greenberger, J. S. Recent Modifications and Technical Improvements in Human Long-Term Bone Marrow Cultures. Proceedings of the Symposium on Long-Term Bone Marrow Culture, Kroc Foundation, September 1983, Alan R. Liss, New York, pp. 119-133, 1984; Greenberger, J. S. The Hematopoeitic Microenvironment. Critical Reviews in Hem/Onc, Elsevier Science Publications B. V. 11:65-84, 1991; Goff, J. P., Shields, D. S., Michalopoulos, G. K., Greenberger, J. S. Synergistic Effects of Hepatocyte Growth Factor on In Vitro Generation of CFU-FM From Human Cord Blood CD34+ Progenitor Cells. Thirty-Sixth Annual Meeting of the American Society of Hematology, Nashville, Tenn., Dec. 1, 1994-Dec. 6, 1994. Blood, 84(10):Suppl. #280A, 1994; Pogue-Geile, K. L., Sakakeeny, M. A., Panza, J. L., Sell, S. L., Greenberger, J. S. Cloning and Expression of Unique Murine Macrophage Colony Stimulating Factor Transcripts. Blood, 85:3478 3486, 1995; Goff, J. P., Shields, D. S., Michalopoulos, G. K., Greenberger, J. S. Effects of Hepatocyte Growth Factor and IL-11 on Human Cord Blood CD34+ Progenitor Cells. International Society for Experimental Hematology Meeting, Duesseldorf, Germany, Aug. 25, 1995-Sep. 1, 1995). Current technologies for the growth of stem cells do not address this problem because these technologies are designed to increase the total number of blood cells, not the number of stem cells per se (Traycoff, C. M., Kosak, S. T., Grigsby, S., Srour, E. F. Evaluation of Ex Vivo Expansion Potential of Cord Blood and Bone Marrow Hematopoeitic Progenitor Cells Using Cell Tracking and Limiting Dilution Analysis. Blood 85, No. 8:2059-2068 (Apr. 15, 1995); Murray, L., Chen, B., Galy, A., Chen, S., Tushinski, R., Uchida, N., Negrin, R., Tricot, G., Jagannath, S., Vesole, D., Barlogie, B., Hoffman, R., Tsukamoto, A. Enrichment of Human Hematopoeitic Stem Cell Activity in the CD34+Thy-1+Lin- Subpopulation from Mobilized Peripheral Blood. Blood 85, No. 2:368-378 (Jan. 15, 1995). Limiting the differentiation of daughter cells is necessary to grow multiple exact replicas of the original stem cells. By identifying in situ the occurrence of cell division and the presence of differentiated cells with microscope imaging, the bioreactor system with z-robot pipette for medium exchange allows solution of this problem: there will be automated exchange of the primary growth medium in a well with a secondary quiescence (i.e., "quieting") medium upon cell division. The first medium promotes proliferation of the original stem cell into exact replicas, and the second medium inhibits differentiation of the resulting daughter cells into committed progenitors.

Understanding and continuing interest in culturing human stem cells obtained from bone marrow and umbilical cord blood has expanded greatly in the last five years. Human stem cell candidates are identified as CD34+Thy1+Lin- (lin-): they express the cell surface antigens CD34 and Thy1 but not lineage specific antigens (lin-). Antigens are molecules on cell surfaces recognized by specific monoclonal antibodies. CD34+ cells in the bone marrow (approximately 1%) can be isolated by immunomagnetic selection (incubating cells with magnetic beads coated with monoclonal antibodies against CD34 and applying a magnetic field). The subpopulation of CD34+ cells (roughly 1 in 2 to 1 in 4) which do not express antigens associated with differentiated or lineage committed cells can also be removed using appropriate antibodies and immunomagnetic selection or by labeling these antibodies with fluorochromes and flow cytometry. The lin- cells obtained after sorting represent around 1 in 50,000 cells from the original population.

Previous work on developing technology for culturing stem cells has focused on hematopoeitic expansion (i.e., solely increasing the number of committed progeny and mature blood cells) rather than increasing the number of uncommitted lin- cells in the population. For example, Stephen Emerson and Bernhard Palsson (University of Michigan, in collaboration with Aastrom Biosciences, Inc.) developed a batch-operated bioreactor for growing large numbers of CD34+ cells in which culture medium is recirculated over a series of layered individual trays on which stem cells are maintained (Van Zant, Gary, Rummel, Sue A., Koller, Manfred R., Larson, David B., Drubachevsky, Ilana, Palsson, Mahshid and Emerson, Stephen G. Expansion in Bioreactors of Human Progenitor Populations from Cord Blood and Mobilized Peripheral Blood. Blood Cells (1994) 20:482-491). Waste and catabolites are removed continuously from the reactor. Modest increases in numbers of CD34+ cells were detected, but the true lineage specificity of the amplified stem cell was not demonstrated (Van Zant, Gary, Rummel, Sue A., Koller, Manfred R., Larson, David B., Drubachevsky, Ilana, Palsson, Mahshid and Emerson, Stephen G. Expansion in Bioreactors of Human Progenitor Populations from Cord Blood and Mobilized Peripheral Blood. Blood Cells (1994) 20:482-491).

Based on the results of previous studies in which modest or no increases in the numbers of CD34+ cells were detected (Van Zant, Gary, Rummel, Sue A., Koller, Manfred R., Larson, David B., Drubachevsky, Ilana, Palsson, Mahshid and Emerson, Stephen G. Expansion in Bioreactors of Human Progenitor Populations from Cord Blood and Mobilized Peripheral Blood. Blood Cells (1994) 20:482-491; Verfaille, C. M., Catanzarro, P. M. W. Li. Macrophage Inflammatory Protein 1α, Interleukin 3 and Diffusible Marrow Stromal Factors Maintain Human Hematopoetic Stem Cells for at Least Eight Weeks In Vitro. J. Exp. Med 1994; 179:643-649), the problem of stem cell differentiation during expansion through a combination of biological and engineering technologies was addressed. It was hypothesized that after one cell division one daughter of the two resulting lin- cells might produce inhibitors which limit proliferation and promote differentiation. This hypothesis suggests that the stem cells will be lost if growth conditions are not optimized—i.e., if the medium is not controlled dynamically to shut down differentiation. This model requires testing with an assay in which individual cell phenotype is identified in situ. By detecting the antigens for CD34, Thy1, and Lin with monoclonal antibodies labeled with different fluorochromes fluorescein isothiocyanate (FITC) and phycoerythrein (PE), it was demonstrated that lineage fidelity can be confirmed while maintaining cell viability. These experiments were conducted in single wells of a 96-well plate.

Achieving the goal of maximizing proliferation (i.e., minimizing the time between cell divisions) and minimizing differentiation of human stem cells clearly requires an automated technology that can significantly reduce the time needed to optimize growth conditions by testing various combinations of the over 30 known molecularly-cloned growth and inhibitory factors. With current tissue culture techniques this task is essentially impossible (Verfaille, C. M. Can Human Hematopoetic Stem Cells Be Cultured Ex Vivo? Stem Cells 1994; 12:466-476).

From a broader perspective, the technology herein will provide a revolutionary means for developing media for tissue culture and protocols for growing cells through the automated testing of a large number of biological variables (e.g., medium composition, environmental conditions, and presence of engineered genes). The opportunity extends into cell biology, molecular biology, the rational development of extracellular matrices for tissue culture and biomaterials, and toxicology. The invention herein will be unique because it enables academic researchers, applied clinicians, or industrial scientists to focus their efforts on understanding the processes of division and differentiation for individual cells. Moreover, the invention herein will be superior to any other available: bioreactors and systems for cell culture which currently are commercially available only allow identification of the properties of populations of large numbers of cells while neglecting phenomena, such as differentiation, which occur at the single-cell level and control the properties of the population.

SUMMARY OF THE INVENTION

The present invention pertains to an apparatus for holding cells. The apparatus comprises a mechanism for incubating cells having a dynamically controlled environment in which the cells are grown, which are maintained in a desired condition and in which cells can be examined while the environment is dynamically controlled and maintained in the desired condition. The apparatus also comprises a mechanism for determining the state of the cells. The determining mechanism is in communication with the incubating mechanism.

The present invention pertains to a method for holding cells. The method comprises the steps of incubating the cells in a dynamically or controlled environment which is maintained in a desired condition and in which the cells can be examined while the environment is dynamically controlled and maintained in the desired condition. Additionally, there is the step of determining the state of the cells.

BRIEF DESCRIPTION OF THE DRAWINGS

In the accompanying drawings, the preferred embodiment of the invention and preferred methods of practicing the invention are illustrated in which:

FIGS. 1b, 1c, 1d and 1e are details of the chamber of a first embodiment of the present invention.

FIG. 2 is a demonstration of the recognition patterns identified by the microscope software which can detect a cell division.

DESCRIPTION OF THE PREFERRED EMBODIMENT

Figure 1A:
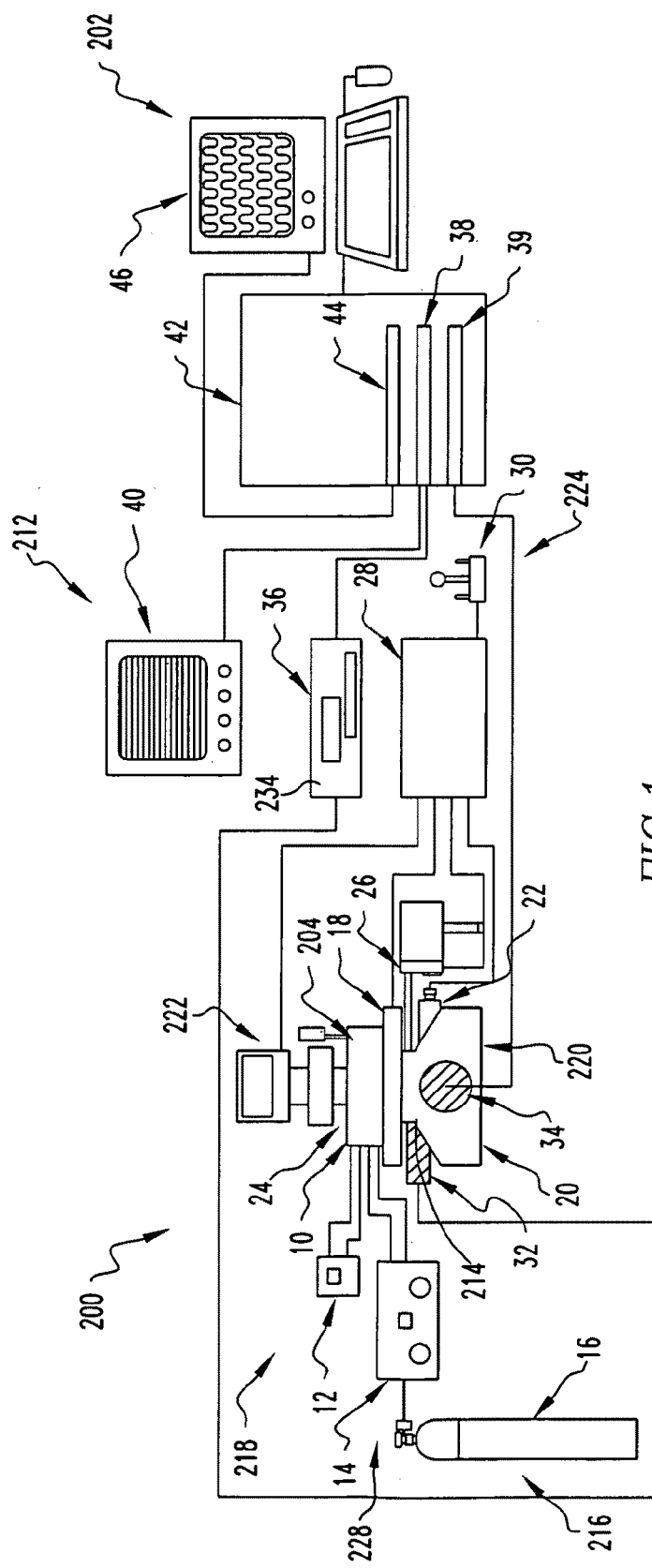
FIG. 1a is a schematic representation of components of a first embodiment of the present invention.
Figure 1B:
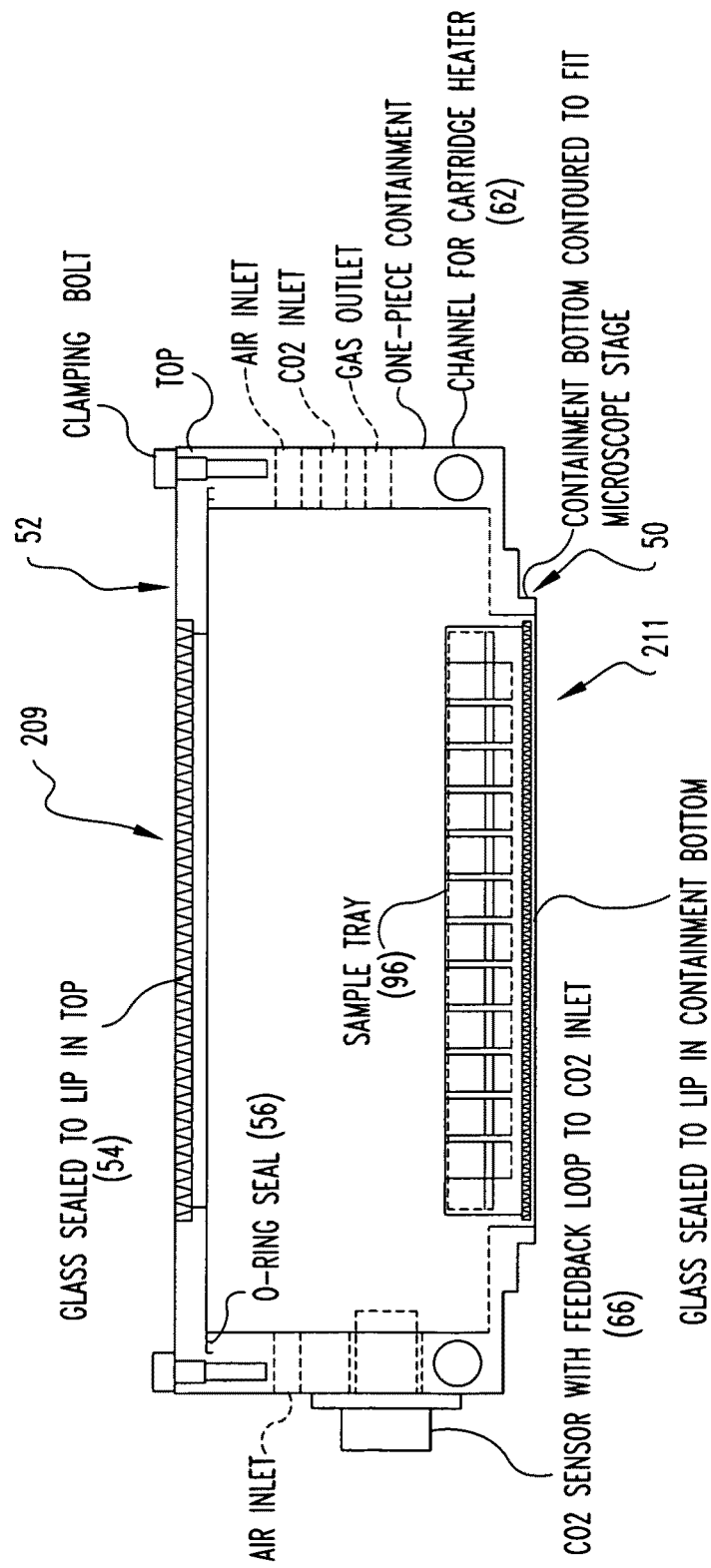
Figure 1C:
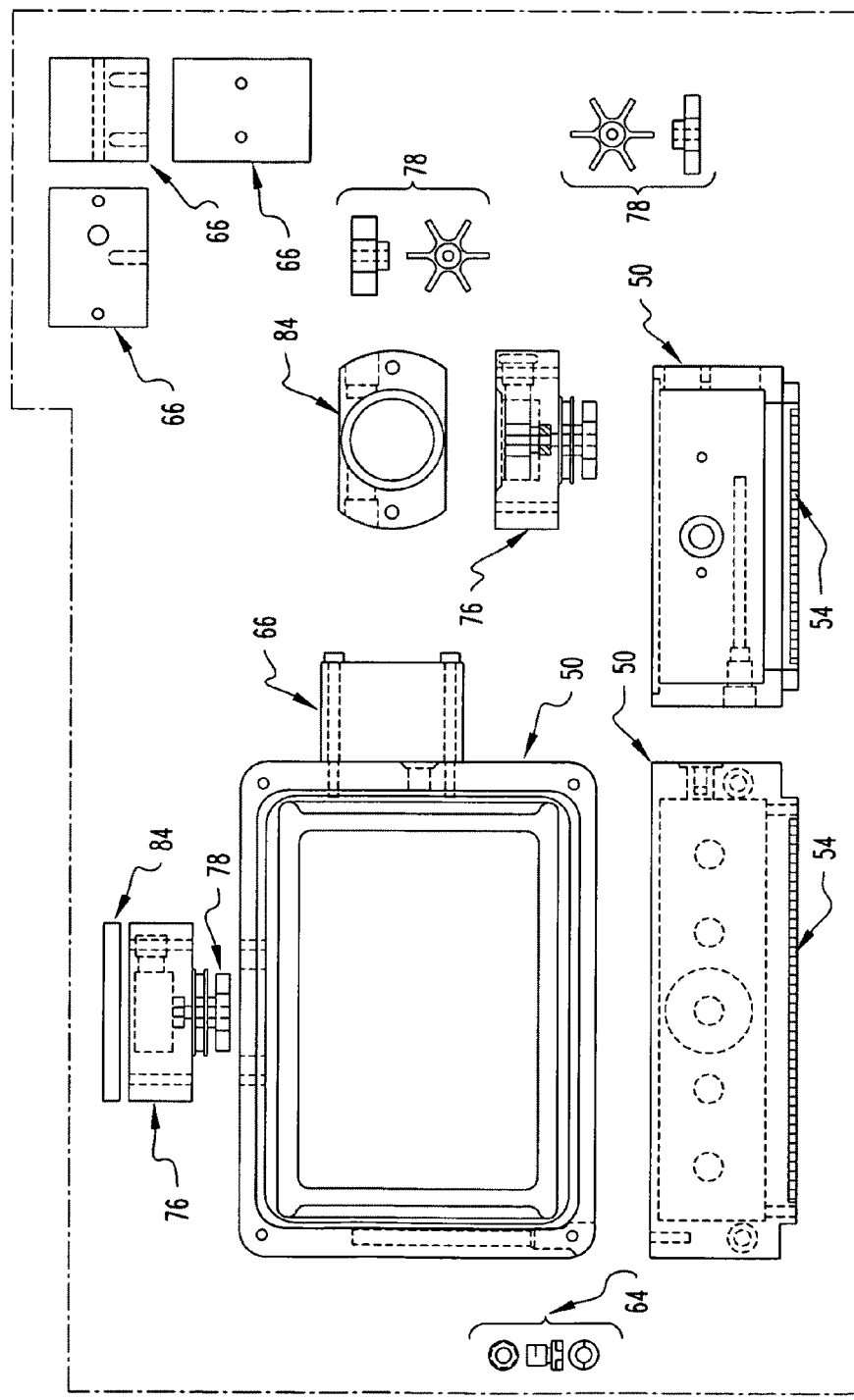
Figure 1A:
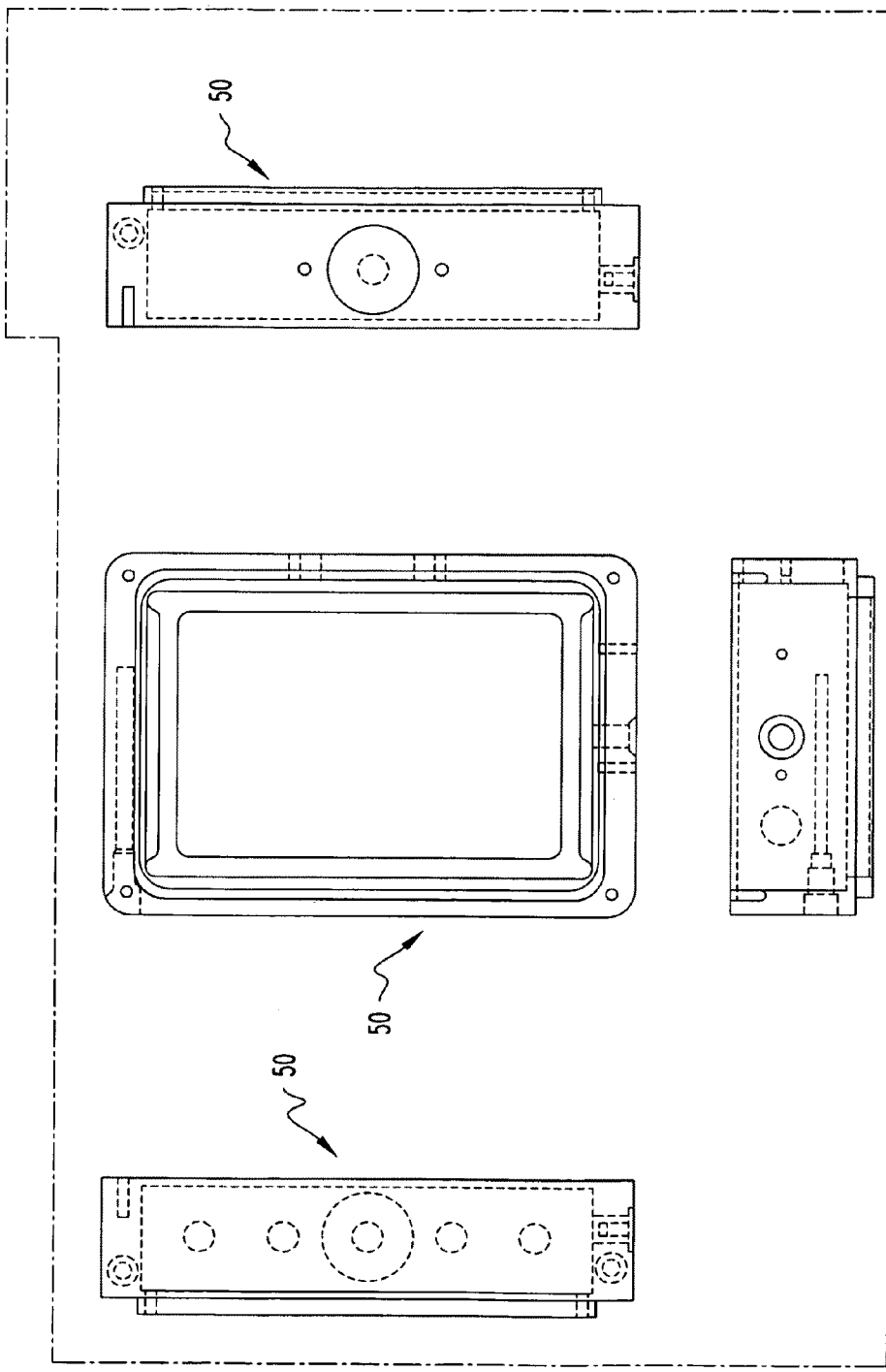
Figure 1E:
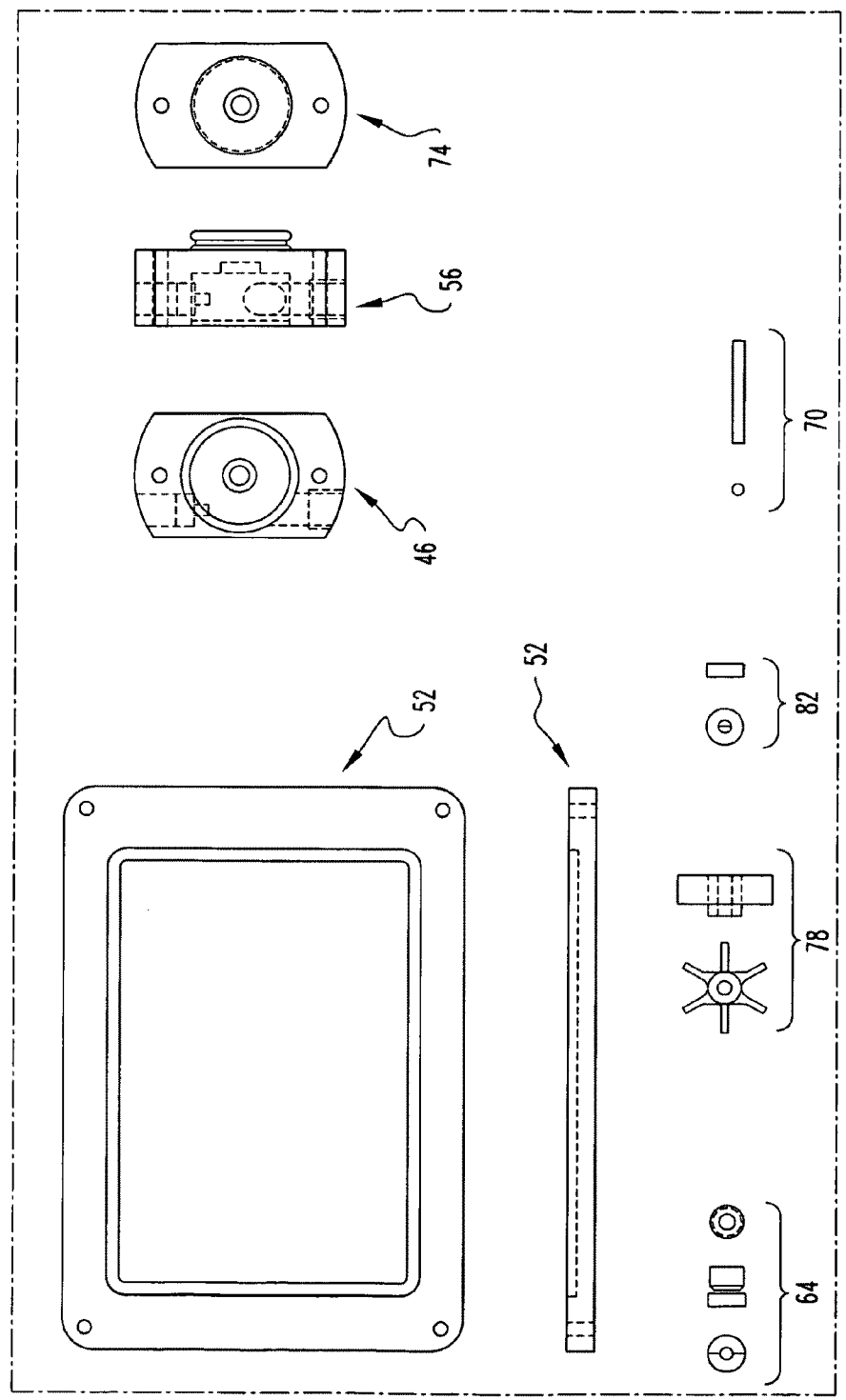

Referring now to the drawings wherein like reference numerals refer to similar or identical parts throughout the several views, and more specifically to FIGS. 1a-1e, 4a and 4b thereof, there is shown an system 300 for holding cells. The system 300 comprises a mechanism 200 for incubating cells having a dynamically controlled environment in which the cells are grown, which is maintained in a desired condition and in which cells can be examined while the environment is dynamically controlled and maintained in the desired condition. The system 300 also comprises a mechanism 202 for determining the state of the cells. The determining mechanism 202 is in communication with the incubating mechanism 200.

The incubating mechanism 200 preferably includes a housing 204 having a Biochamber 10 in the housing 204. The incubating mechanism 200 preferably includes a first well 206 and at least a second well 208 in which cells are grown. The first and second wells are disposed in the Biochamber 10 of the housing 204. The incubating mechanism 200 preferably comprises a transparent plate 207 in which the first and second wells are disposed.

The housing 204 preferably has a first port mechanism 210 through which the first and second wells in the Biochamber 10 can be viewed. The first port mechanism 210 preferably includes a first window 209 disposed in the top of the housing 204 and a second window 211 disposed in the bottom of the housing 204 and in optical alignment with the first window 209 to form an optical path for light entering the first window 209 from outside the housing 204 and to exit the housing 204 through the second window 211. The housing 204 preferably has a second port mechanism 214 in fluid communication with the Biochamber 10.

The determining mechanism 202 preferably includes an imaging mechanism 212 disposed adjacent the first port mechanism 210 which engages the cells in the first and second wells. The imaging mechanism 212 preferably comprises a computer 42 for identifying whether a cell in the first well 206 or the second well 208 has multiplied. The computer 42 is connected to the imaging mechanism 212 to receive images from the first and second wells from the imaging mechanism 212. The imaging mechanism 212 preferably comprises a microscope mechanism 220 which view the first and the second wells. The microscope mechanism 220 is disposed adjacent the first port mechanism 210. The microscope mechanism 220 is in communication with the computer 42. The determining mechanism 202 preferably includes a moving mechanism 224 for moving the first and second wells relative to the microscope mechanism 220 so the microscope mechanism 220 can view the cells in the first and second wells. The determining mechanism 202 preferably includes a joystick 30 connected to the microscope mechanism 220 to control the position of the microscope mechanism 220 relative to the first and second wells. The joystick function can also be controlled directly through computer 42.

The imaging mechanism 212 preferably comprises a camera mechanism 222 for imaging the cells in the first and second wells. The camera mechanism 222 is connected to the microscope mechanism 220 such that the camera mechanism 222 takes images of the cells in the first and second wells through the microscope mechanism 220. The camera mechanism 222 is connected to the computer 42.

Preferably, the incubating mechanism 200 includes a mechanism 216 for controlling the environment in the Biochamber 10. The environment controlling mechanism 216 is connected with the second port mechanism 214. The environment controlling mechanism 216 preferably includes a heating mechanism 218 in thermal communication with the Biochamber 10 to maintain the cells in the first and second wells at a desired temperature. The environment controlling mechanism 216 preferably comprises a mechanism 226 for controlling media pH in the first and second wells in communication with the Biochamber 10, and the environment controlling mechanism 216 preferably also comprises a mechanism 228 for controlling pressure in the Biochamber 10 in communication with the Biochamber 10. The controlling media pH mechanism 228 preferably includes a $CO_2$ controller 14 with tank 16 and sensor 66. The $CO_2$ affects the pH of the media in a well as is well known in the art. The controlling pressure mechanism 228 preferably includes a pressure relief fitting 70 and pressure relief valve 72.

The incubating mechanism 200 preferably includes a robotic mechanism 230 for automatically dispensing and aspirating media to and from the first or second wells. The robotic mechanism 230 includes a reservoir mechanism 232 for fresh and waste media regarding the first and second wells. The determining mechanism 202 includes a diagnostic mechanism 234 in communication with the robotic mechanism 230 for ascertaining an occurrence of a predetermined biological event in the first or second wells.

The biological unit is any type of living organism which divides for reproduction like a prokaryotic or eukaryotic cell such as animal or plant cell including but not limited to:
 a. Single invertebrate cell
 b. Single vertebrate cell
 c. Single parasite organism
 d. Single micro-organism (protozoan, bacterium, trypanosome, amoeba, fungus)
 e. A mammalian cell including but not limited to:
  1. Muscle cell
  2. Fertilized ovum
  3. Glandular cell
  4. Endothelial cell
  5. Immunoreactive cell (T-cell, B-cell, Nk-cell, macrophage, neutrophil, basophil, mast-cell, eosinophil)
  6. Hematopoeitic stem cell
  7. Keratinocyte
  8. Neuron or neural cell including glial cell
  9. Mesenchymal cell or mesenchymal stem cell
  10. Skin cell
  11. Embryonal stem cell
 f. A plant cell including but not limited to:
  1. A cell from a member of the phylum angiospermae (dicotyledoneae, monocotyledmeael)
  2. A cell from a member of the phylum embryophyta (gymnospermae, filicineae, hepaticae, lycopodmeae, equisetineae)
  3. A cell from a member of the class chlorophyta (green algae)

Also, the biological unit can be protozoa, bacteria, single and multicellular organisms, as well as embryonic life forms, including fish, amphibians, reptiles, and all vertebrata. This can also apply to plant cells, as mentioned above, whether they are single-celled such as algae, slime, molds, yeasts, and other small single and multicellular organisms. It is possible that some of these organisms will be important for inserting transgenes to produce recombinant molecules that will be of value in the pharmaceutical or chemical industries, and the Biochamber 10 can be used in all of those kinds of experiments.

The present invention pertains to a method for holding cells. The method comprises the steps of incubating the cells in a dynamically controlled environment which is maintained in a desired condition and in which the cells can be examined while the environment is dynamically controlled and maintained in the desired condition. Additionally, there is the step of determining the state of the cells.

The operation of the preferred embodiment is now described. Concerning biological research, a statistically significant array of single cells can be observed at the individual and descendent levels in real time to ascertain how cellular growth and differentiation are altered by a static or dynamically controlled environment. This capability exceeds that provided by current technologies such as suspension culture coupled with flow cytometry. In such systems, information with good time resolution is unattainable due to hazards or contamination risks associated with breaching the cultivation system for sampling. Additionally, flow cytometry provides population constituent information, but the mother-daughter relationship information is not preserved during analysis. Hence, vital information is routinely lost.

For technologists, the system 300 will enable a more rapid and complete assessment of the synergistic and/or antagonistic effects of different combinations of factors (e.g. hormones, cytokines, radiation, surface treatments, environment, etc.) on cellular proliferation, function, and other metrics. The system 300 allows this purpose to be achieved.

FIG. 1a provides an overall schematic of one embodiment of an automated single-cell culture system; Table I provides a detailed description of the components in FIG. 1a. FIGS. 1b-1e provide a more detailed set of schematics for the Chamber for one embodiment of the automated single-cell culture system 300; Table II provides a detailed description of the components of the Biochamber 10.

A preferable strategy used in the system 300 entails periodic monitoring and analysis of cells housed in 300 μL wells of a disposable, plastic 96-well plate 207 under a sterile, controlled environment using a robotic imaging system (FIG. 1a, 20-46). Cells are observed using an Inverted Microscope 20 with extra-long working distance (ELWD) condenser and phase-contrast objectives and epifluorescence attachments. Digitized phase-contrast images of cells are obtained using a Video-Rate CCD Camera 32 connected to a PixelPipeline Imaging Board 38 installed in a Macintosh Quadra 950 42 through a Time-Lapse VCR 36; the Time-Lapse VCR records images for long-term archiving of image data. Digitized fluorescence images of cells are obtained using a Cooled CCD Camera 34 connected directly to an interface board in the Quadra 950. Imaging operations on the Quadra 950 are performed using Oncor-Image software. Both phase-contrast and fluorescence images are displaced on the Computer Monitor 46 using a Video Board 44 installed in the Quadra 950. Phase-contrast images also are displaced on a High-Resolution Video Monitor 40.

The robotic components of the imaging system (FIG. 1a, 18 and 22-30) are controlled by a Microscope Controller 28 which itself is controlled by commands from the Quadra 950 using Oncor-Image software through a RS-232 interface. The Biochamber 10 is secured on a Motorized Stage 18 mounted on the Inverted Microscope 20. The Motorized Stage 18 has a resolution of 0.1 μm, an accuracy of ±6 μm, and a repeatability of 2 μm. Preferably, the Biochamber 10 itself with Motorized Stage 18 mounts directly on the Inverted Microscope 20. Focus control is achieved for each well using a Motorized Focus Drive Assembly and Controller 22 mounted on the focusing knob of the Inverted Microscope 20. Illumination is switched between transmitted light for phase-contrast imaging and epillumination for fluorescence imaging using a High-Speed Shutter for Transmitted Light 24 and a High-Speed Dual Filter Wheel with Shutter for Fluorescence 26. The Motorized Focus Drive Assembly and Controller 22, the motorized stage 18, the High-Speed Shutter for Transmitted Light 24, and the High-Speed Dual Filter Wheel with Shutter for Fluorescence 26 are connected electrically to the Microscope Controller 28. Initial x-y positioning of the Motorized Stage 18 stage and z-focal planes for each well are chosen using a Joystick 30 connected to the Microscope Controller 28 or by the computer 42.

Cells are maintained in individual wells of 96-well plates under a sterile, controlled environment (i.e., physiological temperature, pH, $pO_2$, and humidity) inside a anodized aluminum Biochamber 10 with glass windows on top and bottom to provide an optical path for imaging. There are two embodiments for the system 300: a Biochamber 10 (FIG. 1a and Table I) and a Biochamber 10 also with z-robot for medium exchange, as shown in FIGS. 4a-4d. The Biochamber 10 for the first embodiment (described in detail in FIGS. 1b-e and Table II) is approximately 6" by 5" by 2" high. Temperature is regulated using a Thermocouple 58, Temperature Controller 12, and Heating Cartridges 62. Media pH is maintained using standard bicarbonate-based buffers and a $CO_2$ Controller 14 which sets atmospheric $pCO_2$ at 5% by regulating the flow of $CO_2$ from a $CO_2$ Supply Tank with Regulator 16 through a solenoid valve based on signals from a detachable $CO_2$ Sensor 66 mounted on the side of the Biochamber 10. Pressure inside the Biochamber 10 is fixed by a Pressure Relief Valve 72. Control of $pO_2$ in the Biochamber 10 can be maintained similarly through a sensor and supply interfaced through two additional chamber frontports. Fast response dynamics and stable control are insured by rapidly mixing the Chamber's atmosphere using a pinwheel turbine 78 driven externally by house air.

Several parts of the Biochamber 10 are maintained in an assembled state at all times. Glass Observation Windows 54 are cemented into the base of the Chamber Body 50 and Chamber Cover 52; the Glass Observation Windows can be removed for replacement but are not routinely because their removal requires breakage. The Thermocouple Fitting 60 is screwed into the right face of the Chamber Body; the $CO_2$ Supply Fitting 68, Pressure Relief Fitting 70, and three Unused Port Plugs 74 are screwed into the front face of the Chamber Body. The turbine is assembled by securing one of the Turbines 78 to the Turbine Shaft 80 with a Brass Bushing 82, screwing the two House Air Fittings 90 into opposing side faces of the Turbine Housing 76, inserting the turbine-shaft assembly into the Turbine Housing such that a Turbine is housed in the Turbine Housing, and securing the remaining Turbine to the Turbine Shaft with the remaining Brass Bushing. Next, the Turbine Housing O-Ring 86 is placed in a groove on the front face of the Turbine Housing, the Turbine Back Plate O-Ring 88 placed in a groove on the back face of the Turbine Housing, the Turbine Housing Back Plate 84 placed on the back face of the Turbine Housing by lining up the groove on the Turbine Housing Back Plate with the Turbine Back Plate O-Ring, and the assembly mounted onto the back face of the Chamber with two 1¼"×³⁄₁₆" hex-nut headed screws. These screws are tightened to form gas-tight seals between the Chamber Body and the Turbine Housing and between the Turbine Housing and Turbine Housing Back Plate.

In operation, before use the disassembled Biochamber 10 is autoclaved with 121° C. steam for 15 minutes for sterility. All components of the Chamber (50-90 in Table II) are sterilized except for the Thermocouple 58, $CO_2$ Sensor 66 and the Pressure Relief Valve 72. The $CO_2$ Sensor and Thermocouple are sterilized by swabbing with a 70% aqueous solution of ethanol in the sterile environment of a laminar flow hood. The sterilized components are removed from the autoclave and placed in the laminar flow hood along with a disposable 96-well plate 207 containing cells. The 96-well plate 207 has been maintained at 37° C. in a humidified atmosphere of 5% $CO_2$ since cells were plated. The procedure for plating cells is described subsequently in this application. Spare wells in the plate in which cells were not plated are previously filled with 100 μL of sterile distilled water to maintain 95-100% humidity inside the enclosed Chamber. The $CO_2$ Sensor is mounted on the right face of the Chamber Body 50 by tightening two 1½"×³⁄₁₆" hex-nut headed screws. The Pressure Relief Valve 72 is connected to the Pressure Relief Fitting 70 with tygon tubing. Next, the plate 207 is placed carefully into the inset on the bottom of the Chamber Body 50 and secured with a spring clip. The Thermocouple is inserted into the Chamber through the Thermocouple Fitting 60 and tightened into place with a Teflon fastener on the Thermocouple Fitting. The Chamber is enclosed by placing the Chamber Cover Gasket 56 in a groove on the top face of the Chamber Body and securing the Chamber Cover 52 in place on top of the Chamber Body and Chamber Cover Gasket by tightening eight 0.50"×0.19" hex-nut headed screws. Chamber assembly is completed by securing the two Heating Cartridges 62 into channels in side walls of the Chamber Body from ports in the front face of the Chamber Body using one Heating Cartridge Retaining Screw 64 each.

Environmental control within the Biochamber 10 is maintained by regulating temperature and the partial pressure of $CO_2$ with two control systems. The Thermocouple 58 is connected by insulated electrical wire to the input junction of the Temperature Controller 12. The two Heating Cartridges 62 are connected by insulated electrical wire to the output junctions of the Temperature Controller. The $CO_2$ Sensor 66 is connected electrically to the input junction of the $CO_2$ Controller 14. The output gas stream from the $CO_2$ Sensor is connected to the $CO_2$ Supply Fitting 68 on the front face of the Chamber and the $CO_2$ Supply Tank with Regulator 16 connected to the input gas stream to the $CO_2$ Sensor. The assembled Biochamber 10 with environmental controls is allowed to thermally and atmospherically equilibrate for one to two hours before placement on the Motorized Stage 18. Temperature and $pCO_2$ are controllable to 37±0.5° C. and 5±0.2%, respectively, over the course of several days.

The Biochamber 10 with environmental controls next is secured on the Motorized Stage 18 with a spring mount. Cells for observation are chosen by scanning wells using the Motorized Stage and Joystick 30 and phase-contrast and fluorescence optics. Image fields of individual wells containing cells for further investigation are selected based on clarity of images. For each well, one or more fields are selected. After selection of fields from up to preferably 96 wells for observation, the user initiates the automated part of the imaging and analysis by selecting the appropriate option. Each field selected then is scanned sequentially at a user-defined interval (preferably between one and 60 minutes). It also is possible to scan at shorter or longer intervals depending on the requirements of a particular biological system. Each field is imaged under phase-contrast optics with transmitted light illumination using the Video-Rate CCD Camera 32 and under fluorescence optics with epillumination using the Cooled CCD Camera 34.

Figure 3:
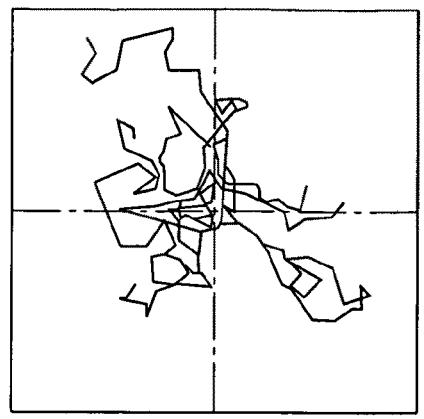
FIG. 3 is a representation of the paths of ten human glioblastoma cells (superimposed to a common origin) over a 12-hour period. Scale bars: 100 μm.

The occurrence of cell division and differentiation is detected by pattern recognition software. The number and two-dimensional shape (e.g., area and perimeter) of "objects" in each selected field are identified from phase-contrast images after application of an optical gradient transformation, thresholding, and dilation to detect "halos" around each cell (see FIG. 2). Threshold values for shape parameters which indicate whether each object is one or more cells have been defined. The number of cells is then determined in each well at that particular time point by comparing the current values of the shape parameters with values for previous time points. Cell division is detected automatically as an increase in cell number between two time points. Image analysis also provides information on (x-y) positions which can be used to measure individual cell speed and directional persistence time by application of a persistent random walk model for migration, to determine the fraction of a population which is motile, and to adjust the position of the field to allow for cell movement while centering cells in the field. The parameter cell speed and directional persistence time for each individual cell and %-motile for a population of individual cells are determined by fitting a mathematical model for a persistent random walk in an isotropic environment to observe data for the mean-squared displacement of each individual cell based on a time sequence of (xyl position at the control of the cell). (DiMilla, P. A., Albelda, S. M., Lauffenburger, D. A., and Quinn, J. A. 1992. Measurement of Individual Cell Migration Parameters for Human Tissue Cells. *AIChE J.* 38(7): 1092-1104; DiMilla, P. A., Stone, J. A., Albelda, S. M., Lauffenburger, D. A. and Quinn, J. A. 1992. Measurement of Cell Adhesion and Migration on Protein-Coated Surfaces. In Tissue-Inducing Biomaterials, L. G. Cima and E. Ron, eds., Mater. Res. Soc. Proc. Vol. 252, pp. 205-212; DiMilla, P. A., Stone, J. A., Quinn, J. A., Albelda, S. M. and Lauffenburger, D. A. 1993. Maximal Migration of Human Smooth Muscle Cells on Type IV Collagen and Fibronectin Occurs at an Intermediate Initial Attachment Strength. *J. Cell Biol.* 122(3): 729-737; DiMilla, P. A. Receptor-Mediated Adhesive Interactions at the Cytoskeleton/Substratum Interface During Cell Migration. In Cell Mechanics and Cellular Engineering, R. M. Hochmuth, V. C. Mow, F. Guilak, and R. Tran-Son-Tay, eds., Springer-Verlag, New York, pp. 490-514, 1994; Thomas, T. W. and DiMilla, P. A. Effects of Substratum Compliance on the Motility, Morphology, and Proliferation of Adherent Human Gliblastoma Cells. In Proceedings of the 1995 Bioengineering Conference, BED-Vol. 29, R. M. Hochmuth, N. A. Langrana, and M. S. Hefzy, eds., ASME, New York, pp. 153-154, 1995), all of which are incorporated by reference herein. Data for the movement of human grade IV SNB-19 glioblastoma cells is depicted in FIG. 3 and demonstrates an application in neuroscience and cancer research.

After completion of an experiment to identify growth or attribute information about a given type of cell, or after cells are grown as desired, the computer program is stopped, the Biochamber 10 removed from the imaging system, and environmental controls disconnected. The Chamber is disassembled in a laminar flow hood. The 96-well plate is saved. The Chamber components are now ready for sterilization and use in a new experiment.

The second embodiment of the system 300 is designed to augment the basic strategy. It implements a different translation strategy in the x-y plane and provides for enhanced diagnostic and growth environment manipulation at the level of a single well in the array.

The second embodiment of the system 300 adds to the features of the first embodiment (continuous non-invasive observation of single cells in multiple wells, sterility, control of temperature to ±0.5° C., control of $pCO_2$ and $pO_2$ to ±0.1%, autoclavablity) with a z-robot pipette that can automatically dispense and aspirate media to and from wells in a 96-well plate. The z-robot thus endows the system with the capability to alter the environment of each well and/or add diagnostic reagents to ascertain the occurrence of biological events or based upon the image recognition of a biological event.

Figure 4A:
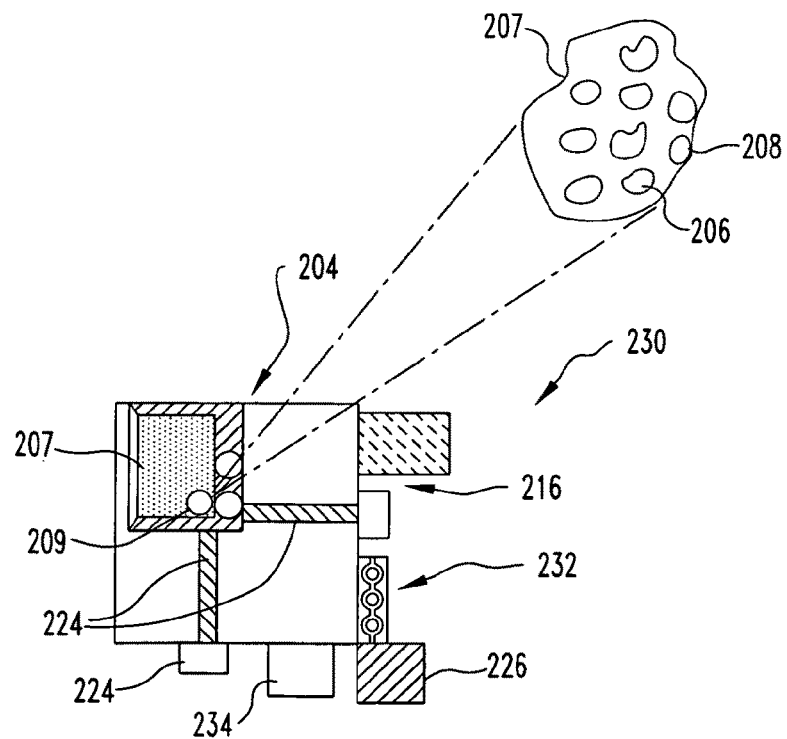
FIG. 4a is an overhead view of a representation of another embodiment of the present invention.

In the second embodiment, the generic motorized stage has been replaced with a custom motorized stage which allows the incorporation of the z-robot pipette. The Biochamber 10 houses a 96-well plate 207 mounted on a movable platter which is moved to specific (x-y) coordinates by a pair of stepper motors. This design moves each well under the microscope objective as well as move any selected well for z-robot pipette servicing. An overview is shown in FIG. 4A.

The z-robot pipette dynamically controls the composition of medium bathing cells to add growth and/or quiescence factors automatically to individual wells based on cell behavior. Software driving the operation of this z-robot pipette is integrated with software for monitoring cell behavior. It also is possible and preferred in some applications of the system 300 to add, remove or change medium based on external criteria, such as at particular time intervals chosen by the user. The z-robot pipette also transfers media from individual wells to supplemental analysis systems.

Figure 4B:
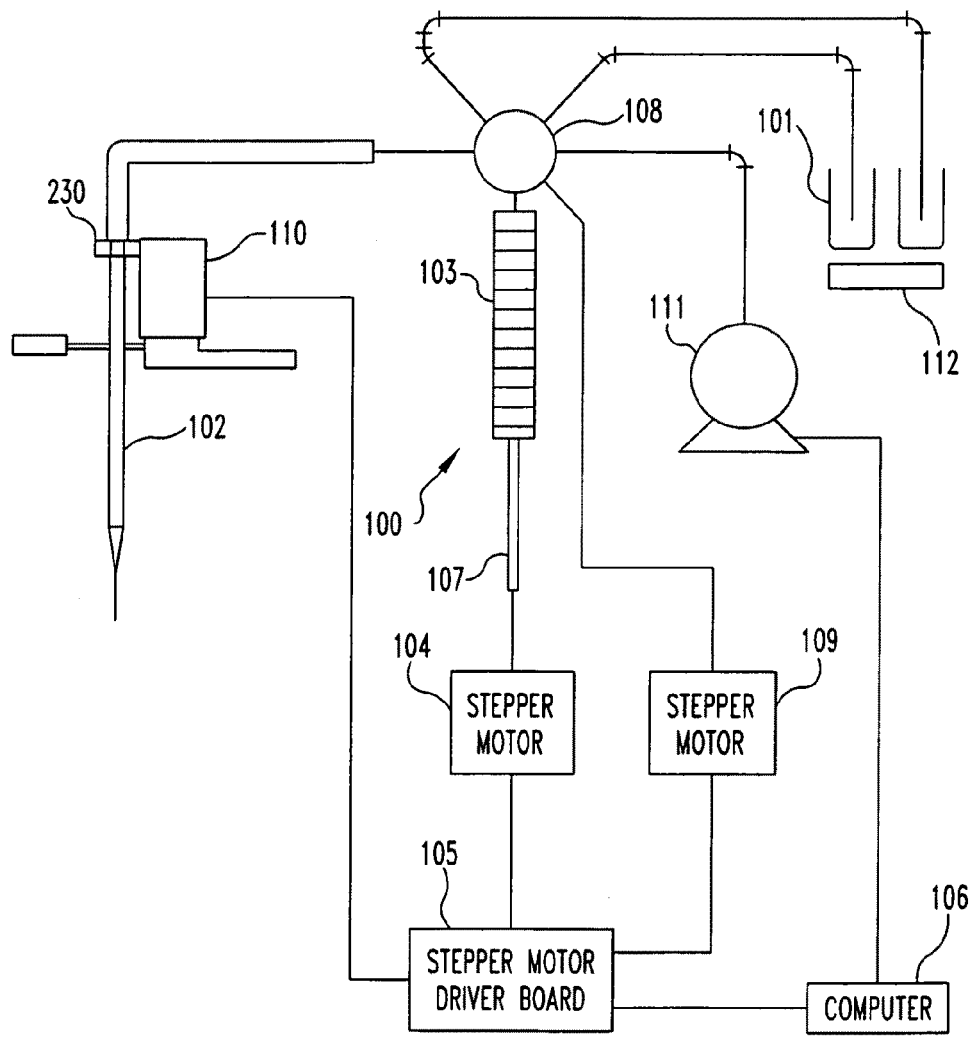
FIG. 4b is a side view of a representation of a z-robot pipette for media change operations.

The z-robot pipette for media exchange itself consists of a modified micropipette tip, see FIG. 4b, mounted on a support arm driven by a z-axis stepper motor to move up and down and raise and lower the pipette tip for aspiration and dispensing media in 1 to 95 µL increments. Note that although typically 100 µL of medium is added to each 300 µL-volume well, aspirating all of the medium from a well will result in very large shears being applied to cells and likely detach or otherwise disturb them. Preferably, the minimum volume of medium which must remain in any well at any time is 5 μL (corresponding to a depth of 125 μm).

Referring to FIG. 4b, the major components of the pipetting system consists of a syringe pump 100 that can deliver growth factors, quiescence factors, or any type of liquid from multiple fluid reservoirs 101 through tubing to a pipette tip 102. The syringe pump consists preferably of a 250 microliter syringe 103 (although other syringe sizes can be used) that is driven by a stepper motor 104, which is in turn controlled via a multi-port stepper motor driver card 105 and a computer 106. The stepper motor 104 drives the plunger 107 of the syringe 103 up and down which results in a dispensing action (if the plunger is being driven into the syringe) or an aspiration action (if the plunger is being driven out of the syringe). The syringe is connected to one port of a distribution valve 108. The distribution valve can be from 3 ports to 8 or more ports. One port is connected to the syringe 103, one port is connected to the pipette probe 102, one port to an optional wash pump 111, and the remaining ports to various fluid reservoirs 101. The distribution valve 108 is also stepper motor driven through stepper motor 109 which can be driven also from stepper motor drive board 105. The syringe, stepper motor, stepper motor driver, and distribution valve can be obtained from Advanced Liquid Handling model MBP 2000 (Williams Bay, Wis.). A second distribution valve can also be mounted in the system in parallel with valve 108 to tie into more fluid reservoirs. The reservoirs 101 are thermostat to 4±2° C. by thermostatting means 112, to allow good preservation of the growth and quiescence medias and tied to the distribution valve 108 through 1/16 inch Teflon tubing.

The distribution valve (and thus the syringe pump) is plumbed via 1/16 inch Teflon or stainless steel tubing to the pipette probe 102. The pipette consists of a stainless steel probe with an ID of 1/32 inch (0.031 inch) that narrows down to a tip ID of 0.013 inch. This pipette tip is used for both dispensing growth and quiescence factors into the 96 well plate as well as aspirating media out of the plate. The pipette probe has conductive coating on the outside of the probe that provides a signal that can be read by the computer 106. This electrical signal provides feedback on how much fluid there is in the well that the probe is in. This is helpful in aspiration to know when no more fluid exists and aspiration should stop. The pipette probe is driven in the "Z" direction by a stepper motor 110 that is tied into the stepper motor drive 105. This stepper motor drives the pipette probe up and down to dispense into or aspirate out of a selected well. The probe with conductive sensing can be obtained from Diba Industries, Inc., (Danbury, Conn.). The pipette stepper motor can be obtained from Advanced Liquid Handling model MBD Crawler (Williams Bay, Wis.). The pipette probe mounts into the biocontainment box by piercing through a Teflon bulkhead. The Teflon bulkhead has a hole in it that is sized to interference fit the OD of the pipette probe. Thus a seal is made between the OD of the pipette and the ID of the hole in the Teflon. This fit allows the pipette to move up and down freely and yet provides a seal to keep the environment within the Biochamber stable. The pipette moves down into the well to a depth of 3±1 mm from the top of the well for dispensing; the pipette moves down to the liquid surface in the well for aspiration (as measured by the conductive sensing mechanism on the probe tip); and the probe moves up out of the well with a clearance of 10 to 13 mm to clear the well as the well plate moves around on the x-y stage.

An alternative embodiment is to have multiple dispensing/aspiration tips so that dispenses to the 96 well plate or aspirations can be done in parallel for higher throughput. A wash is needed with the system to wash out growth factors, quiescence factors or used media from the plumbing lines. The preferred wash fluid is Phosphate Buffer Saline (PBS). One approach is to use one of the reservoirs 101 for wash fluid to clean the system. Another approach is to use a separate wash pump 111 with the system. The wash pump 111 is a peristaltic pump with higher volumetric flow capabilities that can be turned on by the computer 106 and pump through higher flows of wash fluid. The wash fluid is dispensed from the pipette tip 102 to a flush station within the Biochamber 10, as shown by item 330 in FIG. 4d.

Figure 4C:
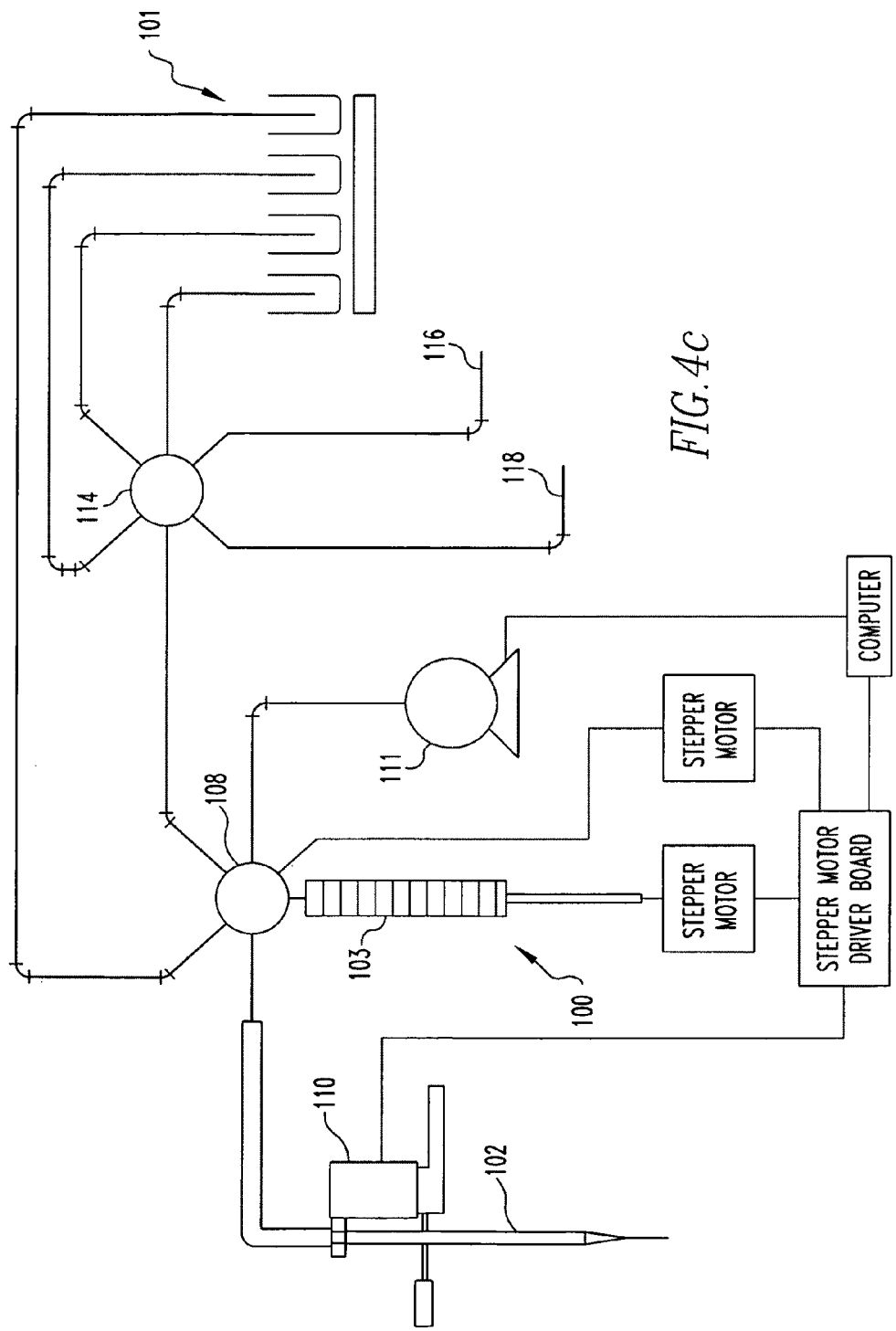
FIG. 4c is a schematic representation of a z-robot pipette with diagnostic elements.

Referring to FIGS. 4a and 4c, various additional analytical determination steps can be added to the system. A second distribution valve 114 has been added to the system and tied into distribution valve 108. This allows more ports to be added to the system. This allows more fluid reservoirs 101 to be added to the system or supplemental analysis systems 116 and 118. These supplemental analysis systems work in the following way: The pipette tip 102 is lowered into a well of the 96 well plate; the syringe pump 100 aspirates out a specific amount of media or fluid from the well through the pipette tip. This fluid is drawn all the way into the syringe barrel 103. The distribution valve 108 and distribution valve 114 is switched so that the flow from the syringe pump is directed out through these two valves to supplemental analysis systems 1 (116) or 2 (118) or to any port connected to the distribution valves. The syringe pump would then pump out through the plumbing and valves to the supplemental analysis systems. These supplemental analysis systems could be any of the following examples, although not limited thereto. Additional supplemental analysis systems can be added based on user requirements.

Tissue culture medium or nutrients removed from individual tissue culture wells by the robotic arm will (for specific experimental uses) be deposited into a protein/nutrient analysis system. Alternatively, all material including cells will be removed for cell counting by automated cell counters (Coulter, Co.). This tissue culture medium can be analyzed by each of a variety of biochemical, immunochemical, biological and chemical assays including but not limited to the following:

1. Radioimmuno-assay for detection of produced hormones such as insulin, growth hormone, prolactin, gastrin, (other peptide hormones) or by radioimmuno-assay for cellular production and release of cytokines including but not limited to: IL-1 (interleukin 1, IL-2, IL-3, IL-4, IL-5, IL-6, IL-7, IL-8, IL-9, IL-10, IL-11, IL-12, IL-13, IL-14, IL-15, M-CSF, GM-CSF, C-CSF, HGF, NGF, basic FGF, acidic FGF, PDGF).
2. Lentil lectin chromatography for detection of glycosylated proteins using columns such as the Sepharose 4β (Pharmacia Corporation) column:
3. Diethylaminoethyl (DEAE) chromatography using a column such as that produced by the Whatman Corporation.
4. Ionic exchange high pressure liquid chromatography (HPLC) analysis using a column such as the Synchropak AX300 column (Thompson Instrument Company).
5. Gel filtration (HPLC), using centriprep or centricon-30 (30,000 molecular weight cut-off) centrifugal microcentrifuge (Amicon Corporation) samples using a column such as the protein-PAK 300 SW (Millipore Corporation).
6. Reverse phase (HPLC), using an apparatus such as the Vydac$C_4$ HPLC column (The Separations Group Corporation) using the equilibration with Trifluoroactic acidic acid, or acetonitrile (made by Pierce Corporation and Baxter Corporation, respectively).

7. Sodium deodecylsulfate/polyacrylamide gel electrophoresis (SDS/PAGE) analysis using commercially available reagents from Integrated Separations Systems Incorporated.
8. Protein analysis for glycosylation by tunicamycin or N-glycosidase treatment (using reagents obtained from Wurthington Biochemical Corporation and Genzyme Corporation).
9. Proliferation stimulation assays (biological assays); aliquots of tissue culture medium will be tested for stimulation of tritiated thymidine incorporation (50-90 MMOL; Dupont Chemical Corporation) by target indicator cell populations with known cell populations that respond to each of a variety of cytokines in each growth factor using published methods. (Pogue-Geile, K. L., Sakakeeny, M. A., Panza, J. L., Sell, S. L., Greenberger, J. S. Cloning and Expression of Unique Murine Macrophage Colony Stimulating Factor Transcripts. Blood, 85:3478 3486, 1995)
10. Respiratory/oxidative physiologic functioning analysis including analysis of pH, bicarbonate concentration, chloride concentration, oxygen concentration.
11. Catabolic product production including assays for ammonium urea, and consumption of glucose, fructose and other sugar molecules contained within the particular culture medium (including Dulbecco's modified Eagles medium, McCoy's medium and other tissue culture media prepared by commercial suppliers and available from GIBCO Corporation or other suppliers).
12. Enzyme analysis including tests for proteases, sucrases, and other sugar conjugating or degrading enzymes using standard biochemical test kits available from SIGMA Pharmaceutical Company, and available in standard hospital clinical laboratories. Assays would include those for amylase, acid phosphatase, alkaline phosphatase, carbonic anhydrase, and others.

The purpose of the assays outlined above will be to determine whether cells identified by the imaging mechanism and Pattern Recognition software and computer analysis system are in a specific physical, chemical or physiological state and to correlate this state with a particular metabolic process including those associated with either production or consumption of the above factors.

In summary, the medium from tissue cultured cells grown in the Biochamber wells would be tested for production or degradation of proteins, simple or complex sugars, individual amino acids, individual ions, and individual molecules, both with respect to physical presence and/or biological activity.

Figure 4D:
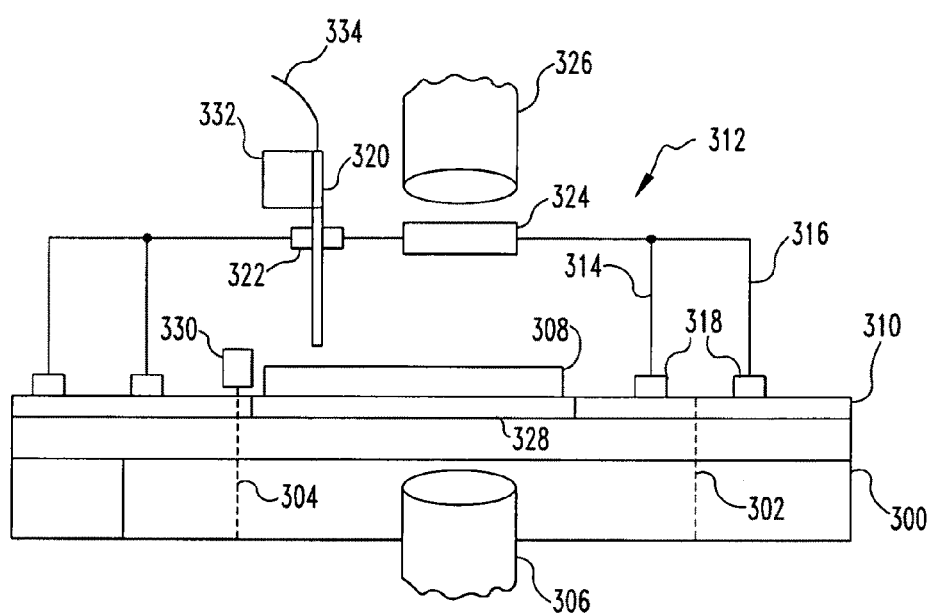
FIG. 4d is a schematic representation of an alternative embodiment of the housing with the chamber of the system.

Another embodiment of the biocontainment box is shown in FIG. 4d, which shows a front view of parts of the system. The X-Y translation system is shown as part 300, which has an open space in the middle of it shown by the dotted lines 302 and 304. This allows the objective lenses 306 to be moved into the X-Y translation table and be focused onto the 96 well plate 308. The 96 well plate 308 is positioned onto a mounting plate 310 which moves according to the translation of the X-Y translation plate. Mounting plate 310 has an optical window 328 in it that is below the 96 well plate. The mounting plate also contains a pipette probe flushing station 330 which is used as a port to flush and clean the probe. The biocontainment box 312 has double walls 314 and 316. Each of these walls is sealed to the mounting plate 310 by a silicone seal 318. The biocontainment box is stationary while the mounting plate 310 moves underneath it. The biocontainment box 312 also has the following parts mounted into it: pipette probe 320 is mounted in a Teflon bulkhead 322 and driven in the Z-axis direction by stepper motor 332; and an optical window 324 is mounted so that light can pass through it into condenser 326 with is positioned above the objective lenses 306, optical window 328, plate 308 and optical window 324. The biocontainment box also has the controls for pH, $CO_2$, humidity, etc mounted into it (not shown). The pipette probe is connected to the syringe pump system via teflon line 334.

The X-Y translation plate moves any well of the 96 well plate over the objective so that the cells in the well can be imaged; it also moves any well to the pipette probe for dispensing or aspiration of media or cells, and it also moves the flushing station to the probe tip so that the probe can be flushed and/or cleaned.

Reservoirs for fresh and waste media, including individual cocktails of growth factors, are located next to the Chamber and maintained at 4° C. Small-volume syringe pumps are used to deliver growth factors and base medium to user-specified compositions, and waste media is aspirated from wells using the same pipette. The pipette is cleaned thoroughly between dispenses and aspirations by flushing with a PBS solution.

The operation of the z-robot pipette has been optimized such that the fluid forces applied to cells are minimized while retaining a sufficient flow rate for rapid medium exchange. The following parameters have been examined: the dynamics and steady-state value of the flow rate, the minimum volume of fluid which must be retained in a well after aspiration, and the effects of locating the nozzle off-center in the well. Medium is dispensed to wells by drop-wise addition. Choosing the optimal parameters for aspiration most quickly is supported by numerical simulations of the fluid mechanics of this process using well-established computational packages (e.g., Fluent). (DiMilla, P. A., Stone, J. A., Albelda, S. M., Lauffenburger, D. A. and Quinn, J. A. 1992. Measurement of Cell Adhesion and Migration on Protein-Coated Surfaces. In Tissue-Inducing Biomaterials, L. G. Cima and E. Ron, eds., Mater. Res. Soc. Proc. Vol. 252, pp. 205-212; DiMilla, P. A., Stone, J. A., Quinn, J. A., Albelda, S. M. and Lauffenburger, D. A. 1993. Maximal Migration of Human Smooth Muscle Cells on Type IV Collagen and Fibronectin Occurs at an Intermediate Initial Attachment Strength. *J. Cell Biol.* 122(3): 729-737; DiMilla, P. A. Receptor-Mediated Adhesive Interactions at the Cytoskeleton/Substratum Interface During Cell Migration. In Cell Mechanics and Cellular Engineering, R. M. Hochmuth, V. C. Mow, F. Guilak, and R. Tran-Son-Tay, eds., Springer-Verlag, New York, pp. 490-514, 1994; Goldstein A. S. and DiMilla, P. A., all of which are incorporated by reference herein.

Overall, the detection of changes in cell phenotype and operation of the z-robot pipette with the features of the first embodiment are integrated. By applying the methodology for phase-contrast imaging to fluorescent images (obtained with a cooled CCD camera) for wells in which fluorescent antibodies against specific antigens for the lin- phenotype are added, the system 300 is able to, for example, identify stem cells from other differentiated cells. As discussed in more detail below, this approach allows one to determine whether and when individual cells differentiate and change phenotype. Kinetic data for the rates of cell division and differentiation can then be obtained. This data is then analyzed using engineering models for probabilistic processes to determine kinetic parameters for rationally optimizing and scheduling changes of media.

A general description of an algorithm for image analysis of a doubling event is now provided. When a cell divides, there are characteristic morphological features that are visible. The pinching of the middle and the swelling of the size, for example. These are used to identify cells that are dividing. In terms of the computer, these events are recognized by changes in the x,y position, area, perimeter, sphericity (a measurement of the closeness to a circle), and eccentricity (a measurement of closeness to a square). Other parameters can be added as new data queue is acquired. Moreover, the trend of these parameters corresponds with the time before the doubling. The parameters are stored in computer memory in a queue for a certain length of time. As new image data is taken, the least recent value is removed from the queue. The trend of this data is compared to the historically known trend that reflects a cell division. If the match is within tolerance, then the computer is signaled that the cell is about to or is in the process of dividing. For example, with stem cells it is theorized that these cells stop moving just before they undergo division. This would signal a decrease in the change of the x,y positions. If the change remains small enough for a significant period of time, then a division may be occurring. However, this alone is not enough to guarantee it, so the trends of the other variables are compared also.

The mathematical nature of the trend comparison is the following. The trend of each parameter up to the point of cell division is curve fitted over a length of time. The current parameters stored in a queue obtained from a cell for a given time period are compared to this smooth curve and the error between the two is calculated. If the error is within a user-specified tolerance, the cell is considered to be approaching a division.

A division could be missed if the cell is not visualized frequently. This could result from having to analyze, stain and/or view other wells or having too many wells to successfully return to each well within a regional period of time. If this is the case, the parameters from the image are compared to the previous parameters. A set of morphological and positional criteria established empirically are used to determine if the two objects could have come from a division or if one additional object all moved into the view field.

Figure 5:
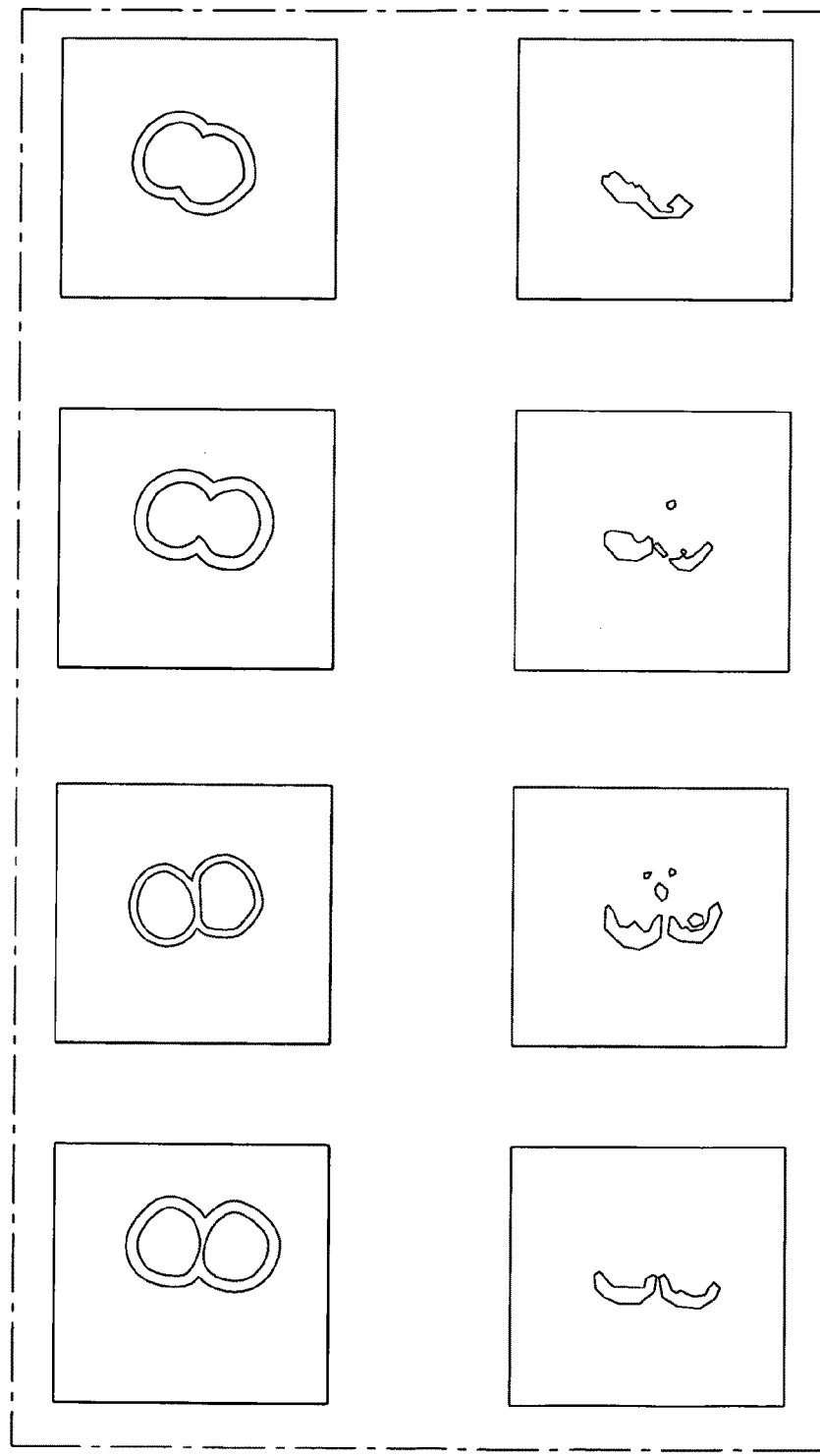
FIG. 5 is a series of photographs showing a stem cell dividing.

FIG. 5 shows the results from an analysis of a cell dividing. The photographs show the phase contrast images on the left and the bitplane pictures on the right. The pinching has already begun to occur in the top left picture.

A protocol for purifying human hematopoeitic stem cells using the system 300 is now provided as an example of using cells generally with the system 300.

Human nucleated blood cells, obtained from either umbilical cord blood, peripheral blood by leukophoresis or bone marrow, are purified free of red cells by centrifugation. Buffy coat leukocytes are then purified to separate CD34+ cells (representing approximately 1 out of 10,000 nucleated cells in human adult bone marrow) using any of several commercially available immunobead, or column chromatography methods. A preferred method is the CellPro Ceprate column, which is commercially available from CellPro Corporation, Bothell, Wash. Using the techniques described in the information supplied by the manufacturer, nucleated cells that are adherent to the column are then washed free from the column by competition with a supply of reagent contained in the package which separates the CD34+ human hematopoeitic cells from the column. This is carried out by competition displacement. The CD34+ cells are washed free through the eluate and are collected. These cells are then sorted a second time using a fluorescence-activated cell sorter and a combination of monoclonal antibodies that are lineage-specific. Those subsets of the CD34+ cells which bind FITC, rhodamine, or other fluorescently labeled indicator of lineage-specific antigens including CD38, are then collected in the lineage-negative (fluorescent antibody-negative) preparation volume. These cells are then prepared for a second FACS (fluorescence activated cell sorting) step, and now are separated into a final population of those reacting positively with a fluorochrome dye for Thy1. This population represents a final concentration of cells which represented one out of 50,000 of the original nucleated cells from the original specimen of peripheral blood, bone marrow or umbilical cord blood. These cells are those known to be highly enriched for multilineage hematopoeitic stem cells. Assays confirming the homogeneity and purification of these cells include the long-term culture initiating cell assay (Sutherland, H. J., Landsdorp, P. M., Henkelman, D. H., Eaves, A. C., Eaves, C. J. Functional Characterization of Individual Human Hematopoeitic Stem Cells Cultured at Limiting Dilution on Supportive Marrow Stromal Layers. Proc Natl Acad Sci USA 87:2584, 1990) incorporated by reference herein), or the cobblestone island assay measuring those cells forming cobblestone islands at day 14 or day 21 after coculture (Ploemacher, R., van der Sluijs, J., van Beurden, C., Baert, M., Chan, P. Use of Limiting-Dilution Type Long-Term Marrow Cultures in Frequency Analysis of Marrow-Repopulating and Spleen Colony-Forming Hematopoeitic Stem Cells in the Mouse. Blood 10:2527-2533; 1991), incorporated by reference herein), or the assay for CFU-blast (Ikebuchi, K., Wong, G., Clark, S., Ihle, J., Hirai, Y., Ogawa, M. Interleukin 6 Enhancement of Interleukin 3 Dependent Proliferation of Multi-Potential Hemopoietic Progenitors. Proc. Natl. Acad. Sci. USA 84:9035; 1987), incorporated by reference herein), or the assay for high proliferative potential colony-forming unit culture [HPP-CFC] (Pogue-Geile, K. L., Sakakeeny, M. A., Panza, J. L., Sell, S. L., Greenberger, J. S. Cloning and Expression of Unique Murine Macrophage Colony Stimulating Factor Transcripts. Blood, 85:3478 3486, 1995), incorporated by reference herein). Each and any of these assays demonstrates that the CD34+Lin-Thy1+ subpopulation of cells is enriched for the presence of cells positive in these assays by a factor of around 1000-10,000-fold. More importantly, these enriched cells have been demonstrated to form multilineage hematopoeitic cells in the peripheral blood in marrow of SCID/Hu mice, or Nu/BIX in xenotransplant studies. These cells have also been shown to reconstitute multilineage human hematopoiesis in fetal sheep (Zanjani, E. D., Almeida-Porada, G. and Flake, A. W. 1995. Engraftment and Multilineage Expression of Human Hematopoeitic Stem Cells in Human-sheep Chimeras. Stem Cells 13:101-111). Thus, by the two xenotransplant models (SCID/Hu mouse, and fetal sheep) as well as the in vitro assays described above, the CD34+Lin-Thy1+ and Thy1− fraction of nucleated peripheral blood, bone marrow, or cord blood cells is known to be highly enriched for stem cells. The phenotype of CD34+Lin-Thy1+ is known to be rapidly lost when cells are cultured in suspension culture as other than single cells and as culture methods other than an automated cell division linked bioreactor (Mayani, Hector, Lansdorp, Peter M. Proliferation of Individual Hematopoietic Progenitors Purified From Umbilical Cord Blood. Experimental Hematology 23:1453-1462 (1995); Van Zant, Gary, Rummel, Sue A., Koller, Manfred R., Larson, David B., Drubachevsky, Ilana, Palsson, Mahshid and Emerson, Stephen G. Expansion in Bioreactors of Human Progenitor Populations from Cord Blood and Mobilized Peripheral Blood. Blood Cells (1994) 20:482-491; Sandstrom, C. E., Bender, J. G., Papoutsakis, E. T., Miller, W. M. Effects of CD34+ Cell Selection and Perfusion on Ex Vivo Expansion of Peripheral Blood Mononuclear Cells. Blood. 86, No. 3:958 970 (Aug. 1, 1995), incorporated by reference herein).

Figure 7A:
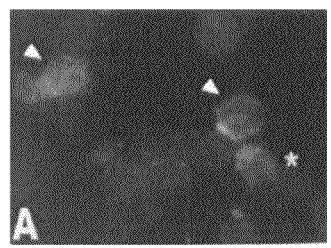
FIGS. 7a and 7b are immunofluorescently stained human umbilical cord blood cells for the expression of CD34, Thy1, and lineage specific markers, respectively.
Figure 7B:
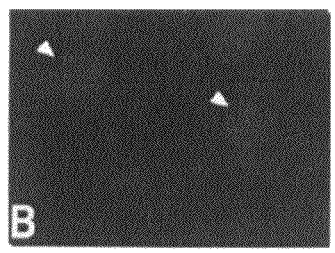

Using 96-well plates (LinBro Plastic Corporation), the MB210 mouse cell line (preferred), or any of a variety of human, murine or primate bone marrow stromal cell lines (or no stromal cell line, or in place of the stromal cell line extracellular matrix protein or proteoglycan such as fibronectin, or heparin sulfate proteoglycan), is plated into each of the 96 wells at $1 \times 10^5$ cells/well in Dulbecco's Modified Eagle's Medium supplemented with 10% fetal calf serum, and the cultures are incubated at 37° C. in a high humidity incubator for 24 hours. The cultures are then removed from the incubator and each well is surveyed to be certain there is a lawn of confluent monolayer of the stromal cell line. The stromal cells are then irradiated to 2000 cGy preferred (1000-10,000 cGy) using a 250 KVP orthovoltage x-ray unit (preferred) or any linear accelerator from 6 MeV-20 MeV with focal plane at the tissue culture surface on the monolayer of cells. The cells are irradiated in the same medium and are returned to the incubator in the same medium. The cultures are then washed free of medium with multiple washes of Iscove's Modified, serum-free medium for each well, and then Iscove's Modified, serum-free medium is added to each well. The exact recipe for the Iscove's Medium is described in the reference (Goff, Julie P., Shields, Donna S., Petersen, Bryon E., Zajac, Valerie F., Michalopoulos, George K. and Greenberger, Joel S. Synergistic Effects of Hepatocyte Growth Factor on Human Cord Blood CD34+ Progenitor Cells are the Result of c-met Receptor Expression. Stem Cells (In Press)), incorporated by reference herein. The serum-free Iscove's Medium (preferred) can be substituted with any commercially available serum-free medium supplemented with vitamins, nutrients, lipid substitute, bovine serum albumin or any of a variety of additives known to support hematopoeitic progenitor cells in the absence of serum, but supplemented with appropriate growth factors. Each tissue culture well is then fed with 100 μL of Iscove's complete medium, and with an additional volume of Medium-A (this is the growth medium and contains optimal concentrations of each of the following growth factors: IL-11, IL-6, IL-1, HGF, G-CSF, basic FGF). This medium will be referred to as growth medium or Medium-A. Each tissue culture well in the 96-well plate is then supplemented with a 10 μL drop containing one FAC-sorted single CD34+Lin-Thy1+ cell, hereafter referred to as "stem cell". The term "stem cell" will be used in this application to refer to a cell with a phenotype demonstrated by fluorescence antibody binding which is positive for CD34+, negative for the lineage markers (the combination of lineage antibody markers used in any of a combination of 10-15 different lineage markers but contains the preferred marker, CD38, and is either Thy1+ or Thy1-). The term "stem cell" will be used to refer to that cell which is either Thy1+ or Thy1- (varies between experiments, preferred Thy1+) but which is definitely CD38- and CD34+. Cells were stained with FITC and PE-conjugated antibodies against hematopoietic cell surface differentiation markers. FIGS. 7A and 7B represent the same field of cells. Examples of cells that are only positive for CD34 and Thy1 appear green (7A, asterisk). Cells that express lineage markers appear red (7B). When the cells are positive for CD34 and Thy1 as well as lineage markers, the wavelengths combine and the resulting fluorescence is yellow (arrowheads FIG. 7A).

The plate of 96 wells containing one stem cell per well is then transferred to the Biochamber 10.

The Biochamber 10 is then closed and the unit is programmed to cycle according to medium change with each cell division (linked to the pattern recognition of the CD34+Lin-Thy1+ phenotype).

Details of the specific motions for each element of the protocol will be described following a short summary. Note that different operational modes are possible and selection depends on, for example, whether the aim is biologic production or more basic investigation. The following summary is a representative production mode where phenotype conservation and high proliferation are intended. An example of operation for basic investigation is presented later in the form of a flow chart.

Each individual well is tracked separately over a cycle of the plate 207 underneath the viewing objective, and this is programmed to be viewed every minute (preferred), can be varied to every 20 seconds or as long as once per day or once per week (or any longer desired length of time) or anything in between. The viewing is accompanied by capture of the image of the cell in the software of the computer linked to the CCD camera. When a pattern associated with a cell doubling is recognized by pattern recognition software, the cell doubling event is recorded and operation of the system 300 linked to the dye recognition phase. The dye recognition phase is activated when the x-y stage moves the well to underneath the z-robot where a combination of fluorescent dyes are added for CD34 and CD38 (lineage marker) as well as for Thy1 (Thy1 marker). After the well is moved by the x-y stage back to the optical path/mechanism and waiting for an appropriate interval (which depends on dye properties), an image is then captured by the cooled CCD camera of the cell doublet with three imaging purposes: 1) detecting the color of the dye on CD34, 2) detecting the color of the dye on the CD38, and 3) detecting the color of the dye on Thy1. The pattern recognition software then recognizes those wells in which a doublet was identified and in which the pattern was noted to be conserved (both cells CD34+ or both cells CD34- to substituting for the latter both cells CD38-) and then the well is moved by the x-y stage to the z-robot which carries out a media change, which will be described in greater detail. The medium is then replaced with Medium-B (quiescence medium) which will be described in greater detail. The entire cycle then continues with observation of that well at regular intervals (preferably each minute, can vary from 20 seconds to more than one week), and then when a second interval has passed (preferably six hours or any time between 1 minute to more than a week), the stage is instructed to translate that well to the z-robot which changes the medium back to Medium-A or growth medium. The entire cycle then repeats again with the pattern recognition software analyzing that well and waiting and scoring for the appearance of four cells. When the presence of four cells have been detected/recorded, the colorimetric fluorochrome staining mechanism of the z-robot adds colorimetric dye, after an appropriate interval (preferably five minutes) more images are taken with the cooled CCD camera and image analysis to detect each of the three fluorochromes, and those wells now which score positive for all four cells with the phenotype of CD34+CD38-Thy1+ are again translated to the z-robot which extracts the Medium-A and replaces the medium with Medium-B. The entire cycle repeats again surveying for the presence of 8 cells, then again surveying for 16 cells, then again for 32 cells, then again for 64 cells, and finally, 128 cells. Alternatively, the system 300 can be operated such that at each cell division (i.e. when 3, 4, 5, 6, . . . up to more than 128 cells are present) medium exchange from Medium-A to Medium-B occurs. When a well contains 128 cells, the imaging protocol is terminated and all the cells (in Medium-B (quiescence medium)) removed from the well into a repository. When the repository is replete with the contents of each well in the plate (representing over 1000 cells), the contents at such repository then are transferred to other parts of the operation for use in gene transfer, bone marrow stem cell transplantation to an awaiting patient, or cryopreservation facility to be used later for gene therapy or for an awaiting patient.

Specifics of the protocol are now provided. The 96-well plate is placed in a sterile tissue culture hood (Format or similar type) and using a Pasteur pipette, the contents of individual 1.0 ml Eppendorf tubes, each containing 10-20 μL of serum-free Iscove's medium which have been supplemented with one sorted CD34+Lin-Thy1+ stem cell, are transferred to each respective well of the 96-well plate. Each well already contains 100 μL of the Iscove's medium, and is now supplemented with 10-20 μL of this medium containing a single cell. The 96-well plate 207 is then transferred to the Biochamber 10. The 100-120 μL in each well contains the concentration of growth factors contained in Medium-A (a range for each of the factors will be included with a preferred concentration indicated: hepatocyte growth factor [HGF], 10 ng/ml-1 μg/ml, preferred 10 μg/ml; IL-11, 1 ng/ml-100 μg/ml, preferred 10 μg/ml; IL-1 10 ng/ml-100 μg/ml, preferred 10 μg/ml; G-CSF, 1 ng/ml-100 μg/ml, preferred 10 μg/ml). Each of these growth factors are available from commercial suppliers including Immunex and Amgen. It should be noted these are but examples of Medium-A or growth medium. There may be many different growth mediums, and not one unique Medium-A, for a given type of cell. An acceptable growth medium is one which allows the cell to reproduce in a healthy manner. The cells are then placed in the Biochamber 10, which is set at a temperature of 37° C. (can be varied from 31° C.-49° C.), and 7% $CO_2$ (can be varied from 0.1% to 40% $CO_2$), and the humidity is kept at a high level (but can be low or very high).

The Biochamber stage is moved so that each well is placed over the microscope objective and in the optical path, and the user moves the stage to identify the exact coordinates of where the single stem cell is located. This is done by hand and usually takes 15 minutes (this can take between one minute and four hours to identify the location of each cell). The coordinates of the individual cell are then recorded and the cycling for observation of the cell is begun with a magnification of 20-40× magnification, preferably 40×. The individual cell is located by image analysis and its position and morphological parameters records by the computer Y2. The computer is then set to cycle to capture the image of the individual well during a six second viewing of this cell (variation between one second and five minutes) using the cooled CCD camera. The time during which the cooled CCD Camera focuses on each well is set to be long enough to capture the image within an acceptable signal-to-noise ratio (preferably 20 seconds, can vary from one second-20 minutes). The digitized image of the single cell in each well is recorded and the stage then cycles over each of the 96 positions (corresponding to one per well) tracking the cellular movement and recording the position of the cell relative to the cross hairs which have been set to define the position of the cell in the initial image capture. The survey of each well is carried out in cycle. The digitized image is recorded sequentially for each well and stored in the computer's memory. The images are compared to one another serially over the time required for one cell doubling to occur in each of the 96 single wells. With the growth Medium-A being in each well, cell divisions are expected to occur in each of the cells within six hours preferably (range can be 10 minutes-two months).

At the time when a cell doubling is detected, as captured by the image at the cycling over that particular well and as reflected in the temporal trends in morphological parameters for the computer's stored set of images and registered as a cell doubling by pattern recognition software, the stage is mechanically moved so that the well corresponding to the cell doubling is underneath the z-robot and fluorochrome dyes are added for determination of the phenotype of the two cells comprising the doublet. The robotic pipette moves down and adds 10 μL (range can be 1 μL-100 μL) of a combination of two fluorochrome dyes including FITC-labeled anti-CD34 and phycoerythrin-labeled anti-CD38. The concentrations of dyes are those as supplied by the manufacturer, and are commercially available. Fluorochromes for detection of each monoclonal antibody (e.g., from Pharmingen, Becton Dickinson, Dakocorp., Immunotech) will be conjugated to each antibody, such that two separate non-overlapping colors, each detected with the appropriate fluorescence filters (available from but not limited to Sigma and Chroma), will be distinguishable and registered by each of two specific images. After the dye has been added to the well with the cell doublet, two successive fluorescent images are acquired with the imaging mechanism consisting of the inverted microscope using epillumination with appropriate excitation filter (placed in the optical path by the High Speed Dual Filter Wheel with Shutter for Fluorescence) and cooled CCD camera and stored as a digitized image on the computer. Each image is exposed for a particular color, either green or red, and for exposure times ranging from 0.1 seconds to 100 seconds. Optimal exposure time for each dye is that determined by the fluorescence intensity of the dye on the cell surface from detection prior to operation of the system 300 and correlated to the positive control test samples for the dye according to manufacturer's instructions. Of the two successive images the first is acquired with a filter that allows imaging of emission in the green range of the visible light spectrum (to detect the binding of anti-CD34 antibody to any CD34 marker present on the surface of the cells of the doublet) and the second acquired with a filter that allows imaging of emission in the red range of the visible light spectrum (to detect binding of anti-CD38 antibody to any CD38 marker present on the surface of the cells of the doublet). This detection scheme is not limited to successive examination for only two distinct colored antibodies and can be extended to detect the presence of additional markers on the cell surface reflecting finer discrimination of cell phenotype. Two types of approaches can be implemented for this extension of detection. In the first, an additional antibody type labeled with a third distinct colored dye other than red or green, such that the emission bands of each of the dyes do not overlap, can be included in the antibody cocktail to detect the presence of a third cell-surface marker. This approach itself allows further extension to fourth, fifth, and more than fifth colors of dyes used to label distinct antibodies against cell-surface markers provided that the emission of each of the dyes can be distinguished unambiguously. In the second approach for extending detection capability of cell phenotype, after acquisition of the initial two successive images using green and red excitation filters, the well is washed sufficiently with PBS and another cocktail containing an alternative set of antibodies labeled with green-emitting and/or red-emitting dyes are added. Again images are acquired successively with green and red excitation filters, respectively. This second approach and the first described approach for extending detection types are not mutually exclusive and can be combined to allow for detection of any desired number of cell-surface determinants by further successive washes and dye-labeled antibody additions. Preferably, the second addition of antibodies will contain a green-labeled anti-Thy1 antibody against Thy1. Each fluorescent image acquired for each distinct dye and antibody will be sorted in computer memory and images overlaid digitally by computer for automated interpretation. Sets of processed images which, with the above approach with successive incubation with anti-CD34, anti-CD38, and anti-Thy1 antibodies, are green positive (i.e., CD34+ and Thy1+ from positive detection of the green dye on cell surfaces in successive green images) and red negative (i.e., CD38− from the absence of red dye on the cell surfaces in the red image) will be recorded and the z-robot will carry out media change. For images of cell in wells not meeting the criteria of green positive/red negative but identified as a cell doublet, a conserved phenotype has not been obtained, and this well will be removed from the survey cycle of image acquisition, pattern recognition, fluorochrome-labeled antibody analysis, and media exchange for the remainder of the process of expanding stem cells. The presence of a non-conserved division indicates that the stem cell phenotype has been lost and that no further increase in stem cell number in this well is possible.

The pattern recognition software and stage movement having registered that an individual well contains two cells with the appropriate phenotype is described above. This well is next moved by the x-y stage underneath the z-robot and 100 μL of media removed, and the waste media placed into the receptacle vehicle in the Biochamber 10. (See FIGS. 4a-4d.) The range of medium removed can be from 10-200 μL (preferred 100 μL). Standard conditions for media change will be those associated with detection of the cell doublet after fluorescence analysis. After withdrawing Medium-A, Medium B containing the quiescence medium will be added. This contains a 100 μL volume of Iscove's Modified Medium, serum-free, as described above but now containing MIP-1α, TGFβ each in the optimal concentration (preferred 10 ng/ml, range 10 ng/ml-100 ng/ml). This quiescence medium is but one example of many possible quiescence mediums. The quiescence medium can simply be a serum-free medium alone added for twenty seconds to five minutes, or a medium with TGFβ or MIP-1α, or TNF. There may be many possible quiescence media that work; that is, which shut down the maturation or differentiation process in the given cell but maintain the cell in essentially a status quo state.

The bioreactor system 300 then continues to cyclically examine all other wells and view this well to which Medium-B has been added as a well in quiescence. A timer within the computer program doing system operations is set to leave the well in which Medium-B has not been added undisturbed, except for imaging for pattern recognition of an additional cell doubling event, for six hours (preferred, range 10 minutes-two months). After the chosen time in Medium-B has passed, this well is automatically returned by x-y stage to underneath the z-robot and again imaged for pattern recognition to identify a cell doublet. Quiescence medium, by definition, facilitates no cell division, and the location of the cells in the doublet as well as their shape will be similar compared to the time when the interval in which the quiescence medium was present began (six hours earlier).

The z-robot then aspirates Medium-B and deposit this medium in the receptacle container within the bioreactor. The z-robot then adds an equivalent volume of Medium-A (the original growth medium). The optimal volume removed of Medium-B is 100 μL, the optimal replacement volume is 100 μL (range can be 10 μL-200 μL).

After addition of Medium-A to the bioreactor well containing two cells, the sequence of review of that well consisting of imaging, pattern recognition, fluorescence analysis and media exchange is resumed. After release of that well from the "quiescence period," routine monitoring at each previously set interval resumes. This interval is as brief as ten seconds, and as long as two months. The well is then assessed for the appearance of four cells (quadruplicates). The pattern recognition software is reset for that particular well to identify a four cell quadruplicate. Upon recognition of the four cell quadruplicate, the well is moved underneath the z-robot and 20 μL of the dye combination added as described above. The same dyes are added in the same concentrations as described above. After an appropriate interval for incubation with the fluorescent dyes (preferred 5 minutes, range one minute-20 minutes), the filters are rotated to image the four cells with the green and red excitation filters, respectively. The exposure times are those as described above. The images are then processed and those wells containing four cells with the (CD34+, green positive, CD38−, red negative) phenotype are then registered as being maintained in the experiment. Those wells containing one or more of the four cells with non-conserved phenotype are eliminated from the experiment. The z-robot then maintains this position over the well with the four cells of conserved phenotype and withdraws 100 μL of Medium-A, replacing it with 100 μL of the quiescence Medium-B as described above. The amount of medium removed and replaced can range from 10 μL-200 μL.

The quiescence media interval is then reset for that particular bioreactor well and the well is left undisturbed, except for routine observation during each cycle for the quiescence interval (preferably six hours, variation two minutes-two months).

the bioreactor system 300 is then reset to indicate that the well will be surveyed for the appearance of eight cells representing an octuplet. The bioreactor system 300 continues to cycle during its observation periods with review of that well at each survey over the 96 wells, and continues its pattern recognition program for 8, then 16, then 32, then 64, then 128 cells. The mechanical and computer algorithms used for identifying increases in the number of cell doublet, the presence of conserved phenotypes, and exchange of media, including scheduling, are as described above, except the threshold number of cells is increased.

When the pattern recognition software recognizes the presence of eight cells in that well, the z-robot adds the previously described concentrations of dyes in each two colors, the imaging devices are used to acquire images of green and red fluorescence, and those wells containing eight cells with the conserved phenotype of green positive, red negative are scored. The z-robot then withdraws 100 μL of growth medium (Medium-A) and replaces it with 100 μL of quiescence medium (Medium-B) and resets the clock for the quiescence interval (six hours preferred, range one minute-two months). Cycling is resumed as described above.

When the pattern recognition software detects the presence of 16 cells in the well, recognition is accompanied by movement of the z-robot to add dye, survey for the green positive, red negative phenotype and then registers those wells in which all cells have the appropriate green positive, red negative phenotype. The z-robot then removes 100 μL of growth medium and replaces it with 100 μL of quiescence medium as described above. That well is then registered as being in quiescence. Cycling is resumed as described above.

The pattern as described above is repeated for those wells containing 32 cells with the green positive, red negative phenotype. The robotic arm moves to this site and withdraws 100 μL of Medium-B and replaces it with 100 μL of the growth medium (Medium-A). Cycling is resumed as described above.

Those wells recognized by the pattern recognition software to contain 64 individual cells then are manipulated as described above such that the z-robot adds the colored dyes and images are acquired using each of the two filters. Those wells containing 64 cells with the green positive, red negative phenotype then have 100 μL of growth medium (Medium-A) removed and 100 μL of quiescence (Medium-B) added. The time interval in quiescence (preferred six hours) will again be re-initiated. Cycling is resumed as described above before replacement of quiescence medium with growth medium.

Pattern recognition software resumes surveying that well in its growth medium until such time as 128 cells are detected in a well. The z-robot then delivers the fluorophore-labeled antibodies and images (with respective excitation filters) for labeled cells in the well. A well containing 128 objects of green positive, red negative is then scored as having achieved the optimum cell division number for that experiment while maintaining the conserved stem cell phenotype. This is the preferred experiment in practice. The number can go up to 256 or higher numbers if this is preferred for the individual experiment in question. Additionally, the plate can have many more than 96 wells and is not limited to such number of wells.

The bioreactor system 300 then removes the growth medium and replace with 100 μL of quiescence medium in this well. The z-robot then harvests all the contents of the well, including the 128 stem cells, and place these in a specific receptacle marked "finished". This receptacle (which may actually be one or more receptacles) is kept in quiescence medium at refrigerator temperature (3° C. preferred, temperature from −270°-37° C.). When 10 "unfinished" wells are obtained containing over 1,200 stem cells, these are taken from the bioreactor system 300 and placed in the "completed" designation receptacle for use in gene therapy, cryopreservation for later use in a patient transplant, or delivered to the physician/clinical group requesting amplified stem cells for a stem cell transplantation.

Figure 6:
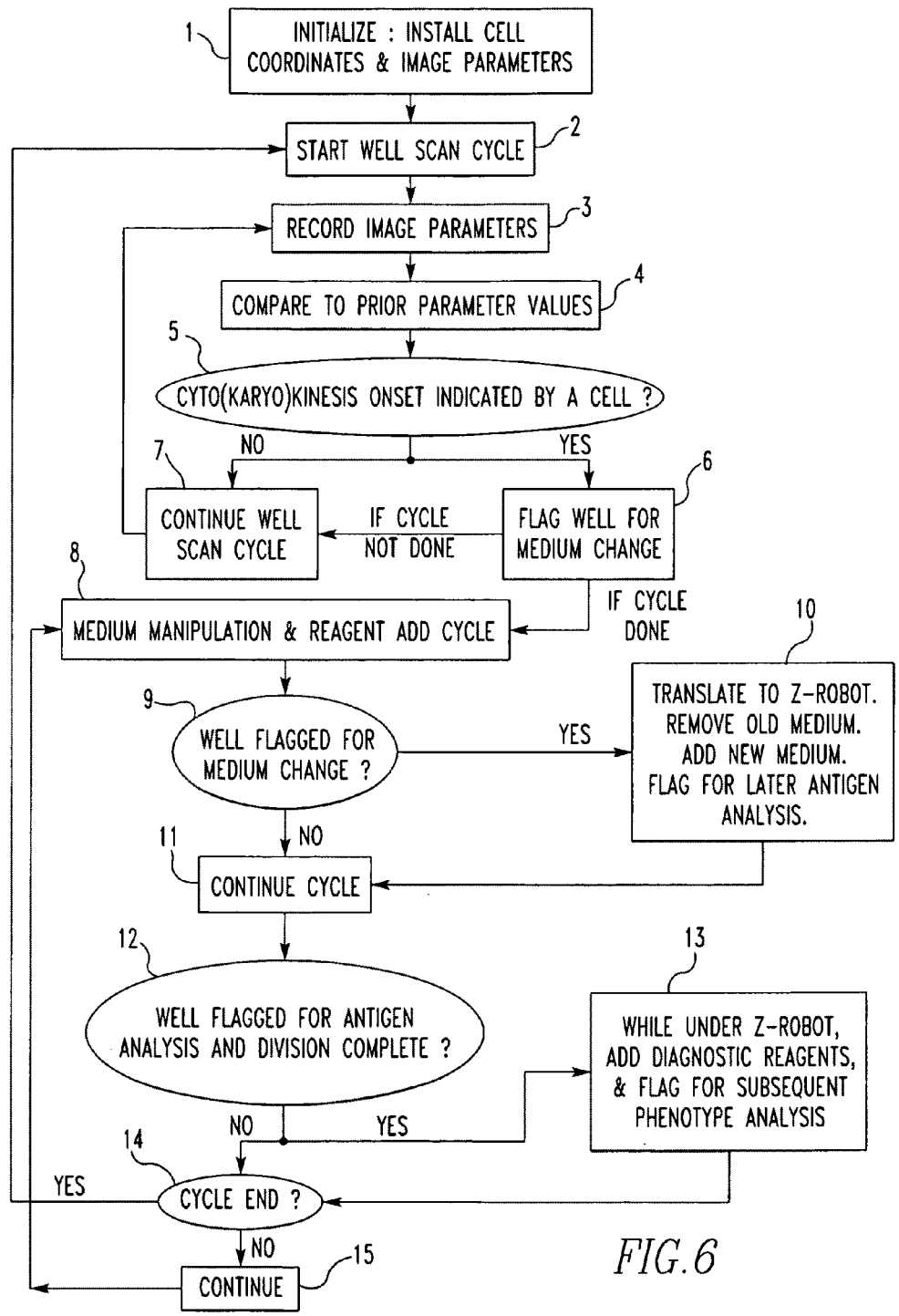
FIG. 6 is a flow chart of the operational mode of the system.

Another example of operational mode is depicted in the attached flow charge, shown in FIG. 6, to illustrate event sequencing and overall system operational integration. The mode shown would allow one to fulfill the goal of recording cellular events in time while manipulating the cellular environment to study response that could, among other things, provide information relevant to directing growth to an optimal target (e.g. prior example). With respect to the enabling technological application, conservation of stem cell phenotype during division, the mode allows for a switch to quiescence medium and a diagnosis of the phenotypic outcome of the first division event. As noted before, other modes are possible.

(1) First the array is initialized; cell coordinates are recorded along with image parameters which have been previously described (e.g. sphericity). (2) Thereafter, the optimal scanning cycle is begun which is in the phase contrast or fluorescence modes. (3,4) The cells in each well are viewed and image parameters acquired and compared to prior values. (5) When the threshold criteria are attained for an event such as cell division, the well is (6) flagged for a medium change. (7) Otherwise, if the scan cycle is not complete (cells in wells remain to be examined), the next cells in the array are viewed, analyzed, and parameters recorded.

When all the cells in the well have been imaged, the (8) medium manipulation and diagnostic reagent addition cycle commences. The stage translates to the z-robot station, and (9) each well in a row that has been flagged as exhibiting a cell starting division is directed under the pipette. (10) The pipette apparatus aspirates old medium and adds quiescence medium; the well is then flagged for subsequent antigen analysis which will be performed after division is complete. (11) If a well is not flagged for a medium change, the (12) need to add diagnostics to a well to enable the determination of cell phenotype is determined before moving on to other wells. The determination is based on being flagged following a prior medium change and being scored as having undergone a division based on the most recently stored image parameters. (13) When flagged for the addition of diagnostic reagents, the z-robot makes the needed additions. The well is then flagged for fluorescence or alternate analysis which will be conducted once the well scan cycle is restarted. (The flagging will automatically engage the needed filters, illumination sources, and relevant sections of the imaging code within the restarted image cycle). (14, 15) This servicing continues until all wells flagged for either medium change or diagnostic addition have been serviced by the z-robot. (Note: the system allows alternate operation where all medium changes are done first, the scan cycle is restarted, and thereafter diagnostic addition is done. This mode is more suited when events are spread in time and parallelizing medium change and reagent addition are not needed). (14) When the z-robot service cycle is complete (YES), the scan cycle is restarted to detect the onset of division or to score the outcome of a division completed in quiescence medium as indicated by the added diagnostic reagents.

The use of the quiescence media is designed as follows:

The transcriptional regulators for cell division can be separated from those associated with adherence and cell differentiation by time. In other words, the addition of specific growth factors sends "three trains down three tracks", by replacing the growth media by quiescence media one train will go to the end of a very small track independently of the effects of more added growth factors (cell division), however, the adherence and cell differentiation trains will stop. Thus, at some point, there are two cells both stopped at the undifferentiated state. By re-addition of growth factors in the growth medium, the three trains are started down three tracks again, by addition of the quiescence media stop trains two and three again. This occurs over and over. Time in the quiescence media will determine whether the cells can recover and be able to start three trains down three tracks. The bioreactor can also be used to determine the length of time in quiescence media to optimize the ideal situation (train 1 goes to completion, trains 2 and 3 stop).

The bioreactor can be used to study cells where there is no a priori information about the cell as follows. Basic tissue culture media such as Dulbecco's modified Eagles medium, RPMI 1640 medium, or other tissue culture liquids available from commercial suppliers is used without any additional serum or growth factors. The subject cells of interest are put in the reactor and the cell shape monitored. If cells are alive their size does not change and they double; if they are dying or experiencing toxicity, their size shrinks and they do not divide. Therefore, the bioreactor can be used first to screen different commercially available medias for what keeps the cell alive (and/or dividing) and then to add different types of serum including fetal calf, horse, goat, or other commercially serum to see what would supplement growth. These parameters would be the same looking at cell size survivability, and division. Then recombinant growth factors such as those listed herein.

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

APPENDIX

TABLE I

Components of Automated Single-Cell Culture System. System is depicted in FIG. 1a.

| Component # | Name | Manufacturer | Description |
|---|---|---|---|
| 10 | Chamber | CMU ChE Machine Shop | Parts described in Table II as components #50-92. |
| 12 | Temperature Controller | Omega | Model CN76000. Input from thermocouple (#58 in Table II); output from two heating cartridges (#62 in Table II) |
| 14 | $CO_2$ Controller | Forma Scientific | Model Portamatic ™. Electrical input from sensor (#66 in Table II) mounted on Chamber (#10). Regulates internal solenoid valve which controls flow of 10% $CO_2$/90% $N_2$ from $CO_2$ Supply Tank with Regulator (#16) to $CO_2$ Supply Fitting (#68 in Table II). |
| 16 | $CO_2$ Supply Tank with Regulator | Matheson (Tank); Regulator (Fisher) | Supplies Chamber (#10) with 10% $CO_2$/90% $N_2$ mixture through $CO_2$ Controller (#14) |
| 18 | Motorized Stage | Ludl | X-Y stage with 4.5" × 3.25" travel. Mounts on Inverted Microscope (#20); motion controlled by 2 each Microstepper Motor Controller Boards 73000500 and Microstepper Power Boards 73000503 installed in Microscope Controller (#28). |
| 20 | Inverted Microscope | Nikon | Diaphot 300, equipped with 100 white light, ELWD condenser, 6-place nosepiece with 4x and 10x phase objectives and 20x and 40x ELWD phase objectives, I1MX-4 lamphouse with Hg bulb, and epifluorescence attachments. Mounts Motorized Stage (#18), Motorized Focus Drive Assembly (#22), High-Speed Shutter for Transmitted Light (#24), High-Speed Dual Filter Wheel with Shutter for Fluorescence (#26), and Video-Rate (#32) and Cooled (#34) CCD Cameras |
| 22 | Motorized Focus Drive Assembly and Controller | Ludl | Model 73000901 Focus Drive Motor Assembly and Model 99A006 Z-axis Control Card. Focus Drive Motor Assembly mounts on focus control of Inverted Microscope (#20) and controls focus through action of Control Card installed in Microscope Controller (#28). |
| 24 | High-Speed Shutter for Transmitted Light | Ludl | Model 99A043 shutter with microscope adapter flange mounts on Inverted Microscope (#20). Position of shutter (i.e., open or close) controlled by Model 73000800 board in Microscope Controller (#28). |
| 26 | High-Speed Dual Filter Wheel with Shutter for Fluorescence | Ludl | Model 99A076 high-speed dual 6 position filter wheel with wheel with 100 ms switching between filters and high-speed shutter for excitation by epifluorescence. Position of filter wheel and shutter controlled by Model 73000800 board in Microscope Controller (#28). |
| 28 | Microscope Controller | Ludl | Model 990082 19" automation electronics console with joystick. Controls movement of Motorized Stage (#18) and Motorized Focus Drive Assembly (#22) and position of High-Speed Shutter for Transmitted Light (#24) and High-Speed Dual Filter Wheel with Shutter for Fluorescence (#26) through communications with Quadra 950 (#42) by RS-232 interface. |
| 30 | Joystick | Ludl | Model 73000362. X-Y action controls sets initial position of Motorized Stage (#18); Z-axis digipot set initial position of Motorized Focus Drive Assembly (#22). |
| 32 | Video-Rate CCD Camera | Hammamatsu | Model C2400-77 High Resolution System with solid-state RS-170 camera head and controller. Mounts on Inverted Microscope (#20); output to Time-Lapse VCR (#36). |
| 34 | Cooled CCD Camera | Photometrics | High performance cooled CCD camera with Kodak Model KAF1400 Grade 1 chip with 1317 × 1035 pixel resolution, and 12-bit/pixel gray scale resolution at 500 kHz and CE200A Camera Electronics Unit controller. Output to Quadra 950 (#42) through NuBus interface board. |
| 36 | Time-Lapse VCR | Sony | Model SVT-5000. Input from Video-rate CCD camera (#32); output to PixelPipeline board (#38) in Quadra 950 (#42). |
| 38 | PixelPipeline Imaging Board | Perceptics | Model 425 with real-time, RS-170 frame-grabber and frame-averaging running Oncor Image ™ software. Input from Time-Lapse VCR (#36); output to High-Resolution Video Monitor (#40). |
| 40 | High-Resolution Video Monitor | Sony | Model PVM-122 12" B&W monitor with 100 lines horizontal resolution. Input from PixelPipeline Board (#38) in Quadra 950 (#42). |
| 42 | Macintosh Quadra 950 System | Apple | Quadra 950 computer with 48 MB RAM, 1 GB harddisk, extended keyboard, and mouse. Connected by |

TABLE I-continued

Components of Automated Single-Cell Culture System. System is depicted in FIG. 1a.

| Component # | Name | Manufacturer | Description |
|---|---|---|---|
| | | | NuBus interface to NuBus Board for Cooled CCD Camera (#34), PixelPipeline Imaging Board (#38), and Video Board (#44). Connected by RS-232 interface to Microscope Controller (#27). |
| 44 | Video Board | Radius | Futura Model LX with 1152 × 870 resolution. Output to Computer Monitor (#46). |
| 46 | Computer Monitor | Apple | 17" Multiscan color monitor. Input from Video Board (#44). |

TABLE II

Components of Chamber for Automated Single-Cell Culture System (Component #10 in FIG. 1a and Table I).

| Component # | Name | Description |
|---|---|---|
| 50 | Chamber Body | Constructed of anodized aluminum. Forms enclosed chamber (#10 in Table I) by assembly with Chamber Cover (#52) and Turbine Housing (#76). Mounts screwed in Thermocouple Fitting (#60) with Thermocouple (#58), 2 Heating Cartridges (#62) secured with Heating Cartridge Retaining Screws (#64), $CO_2$ Sensor (#66) by two 1½" × 3/16" hex-nut headed screws, screwed-in $CO_2$ Supply Fitting (#68), screwed in Pressure Relief Fitting (#70), and 3 screwed-in Unused Port Plugs (#74). Gas-tight seal between Chamber Body and Chamber Cover (#52) maintained by tightening 8 0.50" × 0.19" hex-nut headed screws with Chamber Cover Gasket (#56) in place; gas tight seal between Chamber Body and Turbine Housing maintained by tightening two 1 ¼" × 3/16" hex-nut headed screws with Turbine Housing O-Ring (#86) in place. |
| 52 | Chamber Cover | Constructed of anodized aluminum. Glass Observation Window (#54) glued with silicone rubber into inset. Mounted on top of Chamber Body (#50) of chamber by 8 0.50" × 0.19" hex-nut headed screws. Gas tight seal between Chamber Body and Chamber Cover maintained by tightening screws with Chamber Cover Gasket (#56) in place. |
| 54 | Glass Observation Windows (2) | One each 5.00" × 3.41" × 0.01" optical-grade glass slides glued by silicone rubber into inset on bottom of Chamber Body (#50) and inset on top of Chamber Cover (#52). |
| 56 | Chamber Cover Gasket | Silicone rubber o-ring gasket (size #162) forms gas-tight seal between Chamber Body (#50) and Chamber Cover (#52) with tightening of 8 0.50" × 0.19" hex-nut headed screws. Outer dimensions 6.30" × 4.33", inner dimensions 5.25" × 3.50", thickness 0.01". |
| 58 | Thermocouple | Omega Type K thermocouple. Connected to Temperature Controller (#12 in Table I). Probe extends into Chamber Body (#50) approximately 0.5" above bottom Glass Observation Window (#54). Secured in place by Thermocouple Fitting (#60). |
| 60 | Thermocouple Fitting | Teflon assembly, 1/8 NPT, screwed and sealed with teflon tape into side port on Chamber Body (#50). Secures Thermocouple (#58) in Chamber Body. |
| 62 | Heating Cartridges (2) | 20 watt McMaster-Carr heating cartridge. Each mounts into ports on front of Chamber Body (#50) and secured in place by a Heating Cartridge Retaining Screw (#64). Each connected by insulated electrical wire to Temperature Controller (#12 in Table I). |
| 64 | Heating Cartridge Retaining Screws (2) | One each secures one Heating Cartridge (#62) in sidewalls of Chamber Body (#50) through ports on front of Chamber Body. Constructed of anodized aluminum. Mounts by screwing into Chamber Body. |
| 66 | $CO_2$ Sensor | Copper body containing resistance sensor measuring partial pressure of $CO_2$. Mounted on side of Chamber Body (#50) by two 1½" × 3/16" hex-nut headed screws. Canabalized from components from Forma Scientific Portamatic ™ $CO_2$ sensor. Connected to $CO_2$ Controller (#14 in Table I) by insulated electrical wire. |
| 68 | $CO_2$ Supply Fitting | Teflon elbow, ⅛ NPT, screws and sealed with teflon tape into front port on Chamber Body (#50). Connected by Tygon tubing to $CO_2$ Controller (#14 in Table I). |
| 70 | Pressure Relief Fitting | Teflon elbow, ⅛ NPT, screws and sealed with teflon tape into front port on Chamber Body (#50). Connected by Tygon tubing to Pressure Relief Valve (#72). |
| 72 | Pressure Relief Valve | Georg Fisher Type 360 0.5 psi check-valve. Connected by Tygon tubing to Pressure Relief Fitting (#70) on Chamber Body (#50). |
| 74 | Unused Port Plugs (3) | Stainless steel fittings with threads wrapped in Teflon tape and screwed into unused ports of Chamber Body (#50). |
| 76 | Turbine Housing | Air-tight housing for driving rotation of External Turbine (#78) by flow of house air from input and output House Air Fittings (#90) for atmospheric mixing inside sealed Chamber Body (#50) and Chamber Cover (#52). Constructed of anodized aluminum. Forms enclosed housing with Turbine Housing Back Plate (#84) by mounting on back of Chamber Body with two 1¼" × 3/16" hex-nut headed screws. Gas-tight seal between Turbine Housing |

TABLE II-continued

Components of Chamber for Automated Single-Cell Culture System (Component #10 in FIG. 1a and Table I).

| Component # | Name | Description |
| --- | --- | --- |
| | | and Chamber Body maintained by tightening screws with Turbine Housing O-Ring (#86) in place; gas-tight seal between Turbine Housing and Turbine Housing Back Plate maintained by tightening screws with Turbine Back Plate O-Ring (#88) in place. Turbine Shaft (#82) couples external Turbine (#78) in Turbine Housing to internal Turbine in Chamber Body. |
| 78 | Turbines (2) | Six-bladed impeller constructed of anodized aluminum. Secured on Turbine Shaft (#80) with a Brash Bushing (#82). External turbine housed in Turbine Housing (#76) and driven by flow of house air; internal turbine housed in Chamber Body (#50) and driven by rotation of external Turbine through Turbine Shaft coupling to mix atmosphere inside sealed chamber (#10 in Table I). |
| 80 | Turbine Shaft | Stainless steel 1.16" × 0.125" shaft connecting external and internal Turbines (#78). Each turbine secured on shaft with a Brass Bushing (#82). |
| 82 | Brass Bushing (2) | One each secure external and internal Turbines (#78) to Turbine Shaft (#80). |
| 84 | Turbine Housing Back Plate | Plate allowing assess to inside of Turbine Housing (#76) for assembly and disassembly of turbine unit. Constructed of anodized aluminum. Mounts on back of Turbine Housing with two 1¼" × 3/16" hex-nut headed screws. |
| 86 | Turbine Housing O-Ring | Silicone rubber o-ring gasket (size #24) forms gas-tight seal between Chamber Body (#50) and Turbine Housing (#76) with tightening of two 1¼" × 3/16" hex-nut headed screws. Outer dimensions 1.125" circular, inner dimensions 1.00" circular, thickness 0.01". |
| 88 | Turbine Back Plate O-Ring | Silicone rubber o-ring gasket (size #12) forms gas-tight seal between Turbine Housing (#76) and Turbine Housing Back Plate (#84) with tightening of two 1¼" × 3/16" hex-nut headed screws. Outer dimensions 1.25" circular, inner dimensions 1.00" circular, thickness 0.01". |
| 90 | House Air Fittings (2) | Teflon elbow, 1/8 NPT, screwed and sealed with teflon tape into side port on Turbine Housing (#76). Connected by Tygon tubing to House air supply. |

What is claimed is:

1. An apparatus for incubating and determining the state of individual cells within a plurality of cells comprising:
an incubating mechanism for incubating the plurality of cells, the incubating mechanism is a dynamically controlled closed environment in which the cells are grown and remains closed while it is dynamically controlled, which is maintained in a desired condition and in which each individual cell of the plurality of cells can be individually examined over time while the environment is dynamically controlled and maintained in the desired condition, the incubating mechanism including an environment controlling mechanism for dynamically controlling the closed environment of the incubating mechanism; and
an imaging mechanism for automatically determining the state of said individual cell of the plurality of cells over time disposed in the incubating mechanism while the environment is dynamically controlled and maintained in the desired condition, said imaging mechanism in communication with the incubating mechanism, said imaging mechanism includes a computer for automatically determining the state of said individual cell of the plurality of cells over time.

2. The apparatus as described in claim 1 wherein the imaging mechanism includes a microscope which views said individual cell of the plurality of cells over time in the incubating mechanism, the microscope in communication with the computer.

3. The apparatus as described in claim 2 wherein the imaging mechanism includes a camera for imaging the cells over time, the camera in communication with the computer and microscope so that the camera takes images of the cells through the microscope.

4. The apparatus as described in claim 3 wherein the environment controlling mechanism includes a heating mechanism in thermal communication with the incubating mechanism to maintain the cells at a desired temperature.

5. The apparatus as described in claim 4 wherein the environment controlling mechanism includes a mechanism for controlling media pH in the incubating mechanism in communication with the incubating mechanism.

6. The apparatus as described in claim 5 wherein the environment controlling mechanism includes a mechanism for controlling pressure in the incubating mechanism in communication with the incubating mechanism.

7. The apparatus as described in claim 6 wherein the incubating mechanism includes a robotic mechanism for automatically dispensing and aspirating media to and from the incubating mechanism.

8. The apparatus as described in claim 7 wherein the robotic mechanism includes a reservoir for fresh and waste media for the incubating mechanism.

9. The apparatus as described in claim 8 including a diagnostic mechanism in communication with the robotic mechanism for analyzing media from the robotic portion.

10. The apparatus as described in claim 9 wherein the diagnostic mechanism includes a protein/nutrient analysis system for ascertaining an occurrence of a predetermined biological event of said individual cell of the plurality of cells.

11. The apparatus as described in claim 10 wherein the protein/nutrient analysis system includes an assay for analyzing the cells.

12. The apparatus as described in claim 11 wherein the imaging mechanism includes means for phase contrast imaging to identify the state of said individual cell over time.

13. The apparatus as described in claim 5 wherein the controlling media pH mechanism includes a $CO_2$ controller, tank and sensor for controlling $CO_2$ in the incubating mechanism.

14. The apparatus of claim 1 including a motor that is controlled by the computer and automatically moves the individual cell of the plurality of cells into position while the cell is disposed in the incubating mechanism for the imaging mechanism to automatically determine the state of the individual cell of the plurality of cells over time while the environment is dynamically controlled and maintained in the desired condition.

15. The apparatus of claim 14 including a movable platter disposed in the incubating mechanism that is moved by the motor on which the cell of the plurality of the cells is disposed.

16. The apparatus of claim 15 including a plate having wells having the plurality of cells disposed on the platter and in the incubating mechanism.

17. An apparatus for incubating and determining the state of individual cells within a plurality of cells comprising:
 a housing having a biochamber for incubating the plurality of cells, the biochamber is a dynamically controlled closed environment in which the cells are grown and remains closed while it is dynamically controlled, which is maintained in a desired condition and in which each individual cell of the plurality of cells can be individually examined over time while the environment is dynamically controlled and maintained in the desired condition, the biochamber including an environment controlling mechanism for dynamically controlling the closed environment of the biochamber; and
 a protein/nutrient analysis system for automatically determining the state of said individual cell of the plurality of cells over time disposed in the biochamber while the environment is dynamically controlled and maintained in the desired condition from media in the biochamber, said protein nutrient analysis system in communication with the biochamber, said protein/nutrient analysis system includes a computer for automatically determining the state of said individual cell of the plurality of cells over time.

* * * * *